US008293118B2

(12) United States Patent
Miller et al.

(10) Patent No.: US 8,293,118 B2
(45) Date of Patent: Oct. 23, 2012

(54) DEVICE AND METHOD FOR TREATMENT OF CANALS

(76) Inventors: John C. Miller, Fresno, CA (US); Deborah L. Miller, Fresno, CA (US)

( * ) Notice: Subject to any disclaimer, the term of this patent is extended or adjusted under 35 U.S.C. 154(b) by 406 days.

(21) Appl. No.: 12/657,273

(22) Filed: Jan. 15, 2010

(65) Prior Publication Data

US 2011/0079559 A1 Apr. 7, 2011

Related U.S. Application Data

(60) Provisional application No. 61/248,165, filed on Oct. 2, 2009.

(51) Int. Cl.
*C02F 1/76* (2006.01)

(52) U.S. Cl. ..................... 210/747.5; 210/756; 210/764; 210/241; 222/1; 222/4; 222/394

(58) Field of Classification Search ............... 210/747.5, 210/747.6, 756, 764, 170.1, 199, 241, 242.1; 405/118; 222/1, 4, 195, 394, 399
See application file for complete search history.

(56) References Cited

U.S. PATENT DOCUMENTS 6,817,541 B2 * 11/2004 Sands et al. .................. 210/760

* cited by examiner

*Primary Examiner* — Lucas Stelling
(74) *Attorney, Agent, or Firm* — Joan I Norek; The Law Office of Joan I. Norek

(57) ABSTRACT

A method of treating an agricultural-water canal to decompose organic debris in the agricultural-water canal is disclosed. The method provides a controlled delivery of biocide particles to the surface of water by entraining biocide particles in a gaseous stream and then scattering the biocide particles across the surface of the water by propelling the biocide-laden gaseous stream to the surface of the water, whereat the biocide particles are released from the gaseous stream. A device for implementing the method is also disclosed. The device includes a gas blower, a feed hopper and a port which is adapted to direct and propel the biocide-laden gaseous stream to the surface of water in the agricultural-water canal.

15 Claims, 9 Drawing Sheets

DEVICE AND METHOD FOR TREATMENT OF CANALS

CROSS-REFERENCE TO RELATED APPLICATIONS

The present application claims filing date priority under 35 U.S.C. 119 based on copending U.S. provisional application No. 61/248,165 filed on Oct. 2, 2009.

BACKGROUND OF THE INVENTION

Canals, aqueducts, and the like, particularly when combined into systems, are typically used to deliver water to agricultural growers for agricultural purposes, particularly for irrigation. They are the primary water-delivery and water-storage systems in many regions. These agricultural-water canal systems are generally open to the atmosphere along most of their extensive lengths. Because of this great exposure to the atmosphere, these canal systems are extremely susceptible to being, and normally are, inoculated or contaminated with air-borne biologicals such as algae. Further, biological contamination of the water reservoirs or other bodies of water that feed agricultural-water canal systems is not unusual, and in such circumstances there is a substantially continuous or repeated loading or charging of biological contamination to the canals.

These agricultural-water canal systems are, as mentioned above, open to the atmosphere along most of their extensive lengths and, further, they are normally accessible from the land along at least some stretches. The canal systems therefore are routinely additionally polluted with macro-biological materials such as aquatic flora, and biological and biologically-derived debris and waste, which ultimately also increase and/or intensify the biological and biologically-derived contamination. Additionally, agricultural wastes, most notably fertilizers and/or soil amendments from adjacent agricultural lands, are commonly flushed to into the canals from the adjacent filter stations belonging to the agricultural grower.

With urban areas expanding into rural areas, water storage areas such as the canal systems are also being polluted by urban wastes, including without limitation fertilizers, organic products, and municipal wastes that are treated and diluted, and then released into agricultural-water canal systems. These nutrient sources contribute to the proliferation of biological build-up in the canal systems. Further, such urban-waste material can itself constitute canal-fouling organic debris if incompletely and/or insufficiently treated and diluted before release.

The microbiological contaminants ("microbials") from these and possibly other sources propagate and flourish in the typical agricultural-water canal environment. In contrast, the water from an incoming water-delivery system, such as a canal, that is targeted for human uses in urban areas is typically treated by the municipality at a regional water treatment plant, and the water is then sanitarily piped to the consumer. For agriculture uses, however, the water-delivery systems (which routinely are canal systems) extend across vast areas of land as above-ground systems which are open to the atmosphere and accessible from the land, and therefore susceptible to biological contamination as described above. The typical canal system for agricultural uses runs to many miles in length, transports water to multiple water-delivery points along its length, and has varied water-flow rates which are sometimes very low or stagnant.

The typical canal system and its management pose unique problems and challenges, and are in turn beset by a number of adverse circumstances, including without limitation the increasing demand for not merely agricultural water but for unadulterated, or less adulterated, agricultural water. The demand for agricultural water increases with population increases because greater populations have higher agricultural crop requirements, and greater agricultural crop output requires higher irrigation water consumption. The agricultural-water canals must be kept free from macro-biological fouling, and aquatic weed growth (to which algae clings) along the canal must be minimized to keep the water of a canal free-flowing. The treatment of the canals to keep them free flowing is usually conducted on behalf of water districts which are formed to manage water distribution to growers in a particular region or district. (The water districts normally manage and distribute water from a state and/or federal aqueduct system, via the canals, to the growers within the district.)

The individual growers want the water supplied via a water-district canal or, in some instances usually associated with the larger growers, via private canals, to be sufficiently uncontaminated so that it does not plug or foul their intake screens along the canal which are upstream of their pumps or other filters.

Another canal-system problem which is created or aggravated by biological-debris contamination is the plugging of the canal system itself. The flow of water in a canal system is normally gravity driven, that is, the water flows forward in the canal system because it is moving from one elevation to a slightly lower elevation. This gravity-driven water flow is not particularly dynamic, and it normally is not sufficiently fast or forceful to demolish blockages, obstructions and the like in the canal system, or even to prevent a blockage-creating build-up of organic debris. When a section of a canal system becomes plugged with organic debris, the effect is analogous to a log jam (although the plugging material is organic debris such as algae). Such plugging typically, but not always, occurs where the canals run through underground culverts or pipes below road crossings. The water, or at least a large amount of the water, does not flow past the plugged section, and the continued forward flow of water creates a back-up of water upstream of the plugged section. The backed-up water generally will then overflow the banks of the canal system, which typically damages the canal system itself and/or surrounding environs, such as nearby agricultural lands.

Frustrating the pressures for cleaning up canal-system water are governmental regulations concerning canal-system treatment. These regulations are becoming increasingly restrictive and stringent for a number of reasons, including without limitation the ever-increasing proximity of general-population areas to agricultural areas and widening concerns about the water quality of rivers and oceans into which canal systems ultimately discharge their undistributed waters. The use of two types of canal-system water treatment chemicals have been under ever-increasing regulatory pressures. These chemicals are chlorine gas and a commercial product sold under the Magnacide® trademark. (Magnacide® is a federally-registered trademark for bactericides, biocides and herbicides of Baker Hughes Incorporated of Houston, Tex., as assignee of Magna Corporation of Santa Fe Springs, Calif.) The use of chlorine gas presents a risk of a deadly gas release into the atmosphere. The commercial Magnacide® treatment chemicals, and in particular the commercial Magnacide® b microbiocide (U.S. EPA Product Registration No. 010707-10) contains, as its active ingredient, acrolein, at a level of 95 percent by mass. The commercial Magnacide® b microbiocide has a U.S. EPA Restricted Use status (use only by, or under direct supervision of, a certified pesticide applicator) and a toxicity code of 1, which corresponds to a toxicity category of Danger. The commercial Magnacide® h aquatic herbicide (U.S. EPA Product Registration No. 010707-0) has the same 95% acrolein content and the same Restricted Use and toxicity code 1 ratings as Magnacide® b microbiocide.

Acrolein, which is also known as acrylaldehyde, acrylic aldehyde and allyl aldehyde, is an extremely toxic poison and all human exposures thereto, including exposure by inhalation, skin contact, eye contact and ingestion, require medical attention. Acrolein has a high water solubility of 238,000 mg/L, an adsorption coefficient (ability to bind to soil) ($K_{oc}$) of 0.76, a hydrolysis half-life of 2.04 days, an aerobic soil half-life of 0.16 days, and an anaerobic soil half-life of 6.22 days. Acrolein is listed as a potential groundwater contaminant by the state of California because of its potential to move into ground water based on its water solubility, ability to bind to soil and half-life, all of which characteristics are described above. Acrolein is a toxic air contaminant and as a pesticide is deemed toxic to fish and wildlife. As to specifically its aquatic ecotoxicity, mortality is one of its toxic effects on amphibians, annelids, aquatic plants, crustaceans, fish, insects, mollusks, nematodes, flatworms and zooplankton. As to its average acute toxicity, acrolein is very highly toxic to amphibians, highly toxic to fish, mollusks and zooplankton, and moderately toxic to crustaceans and insects. Acrolein is highly reactive chemically. It can violently react if brought into contact with alkalis or acids and it cannot be used or stored near fire, sparks or heated surfaces.

Copper sulfate and chelated copper products have also become disfavored for aquatic pesticide use due to their high cost and the potential for heavy metal build-up in the agricultural soils receiving irrigation water from canal systems which have been so treated.

Because of the tightening of governmental regulations, and because of the toxicity issues underlying these regulations, the algae and other organic debris problems in many canal systems now are often only being managed by mechanical harvesting, that is, the physical or mechanical removal of these contaminants. This method is costly because it is labor intensive, and it is an inferior approach to canal-system management because only large patches or growth areas of contamination are removed. Reseeding, regrowth and post-removal contamination proliferation are common because complete physical removal, particularly complete physical removal of microbials, is not possible.

For these reasons, there is a serious and long-felt need for an effective, economical, and environmentally sound treatment for, and method to treat and/or remediate, canal systems to eliminate the organic-debris contamination and build-up thereof in canal systems.

SUMMARY OF THE INVENTION

The present invention is a method for the delivery of a treatment chemical (preferably calcium hypochlorite), in a solid form, to the surface of the water of a canal by propelling a gaseous stream (preferably an air stream) in which the treatment chemical is entrained. The present invention is also a device for the practice of such method. The method of the present invention, particularly when practiced using the device of the present invention: (a) can, and preferably does, treat the entire surface of a canal; (b) can be, and preferably is, variable so that higher dosages are delivered to areas of higher organic-debris infestations; (c) is not deleteriously impacted by low water flow conditions; and (d) in preferred embodiments, impregnates organic-debris masses, such as algae mats, and therein slowly releases chlorine from within for more effective decomposition of the surrounding mass.

DETAILED DESCRIPTION OF THE INVENTION

Figure 1:
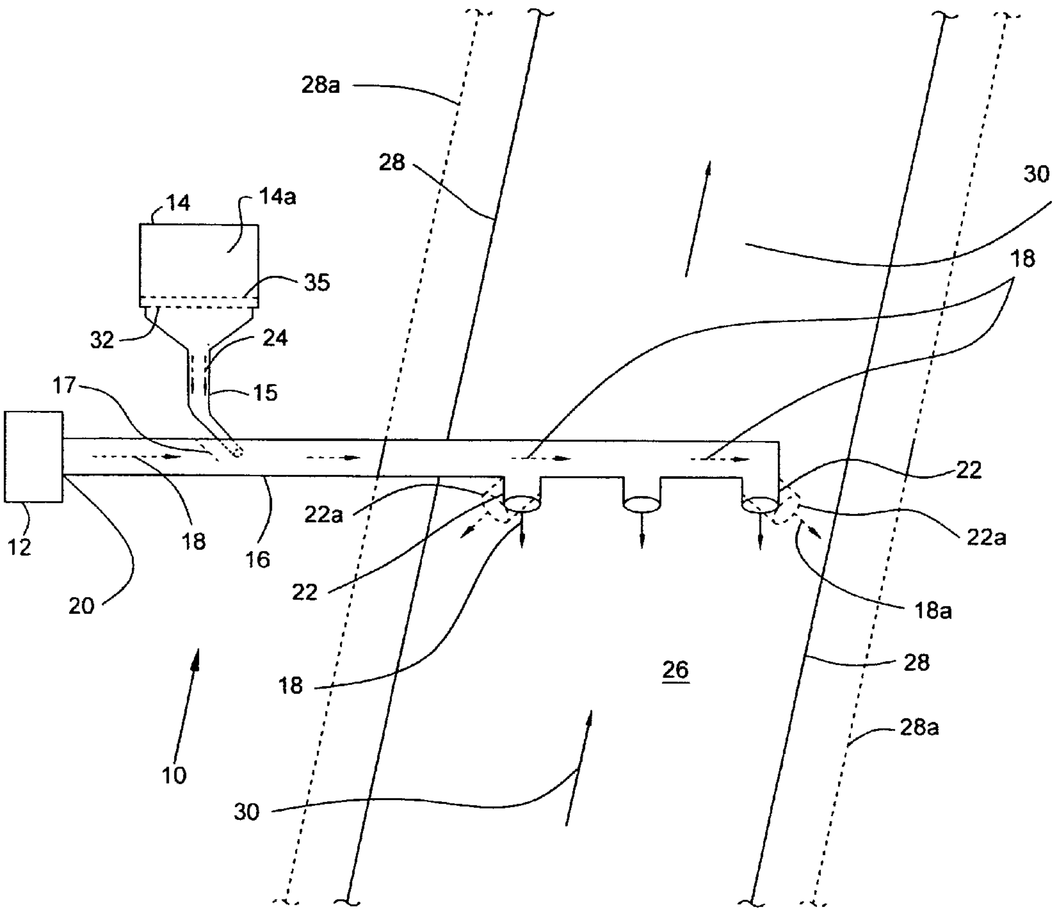
FIG. 1 is a partially diagrammatic perspective view of a delivery system of the present invention extended out across a canal.
Figure 1A:
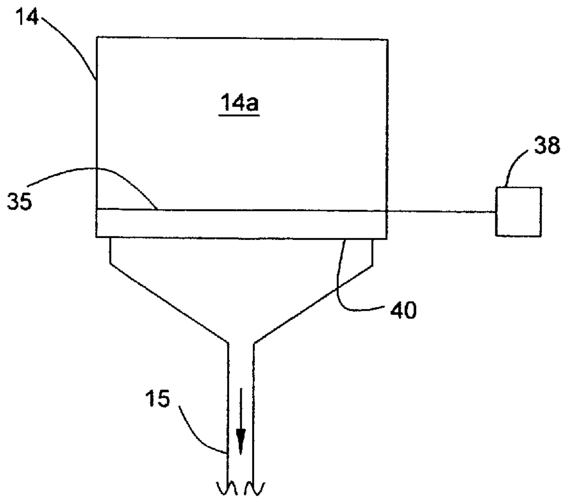
FIG. 1*a* is a partially diagrammatic cut-away front view of a feed hopper and its tail member of the delivery system shown in FIG. 1.
Figure 1B:
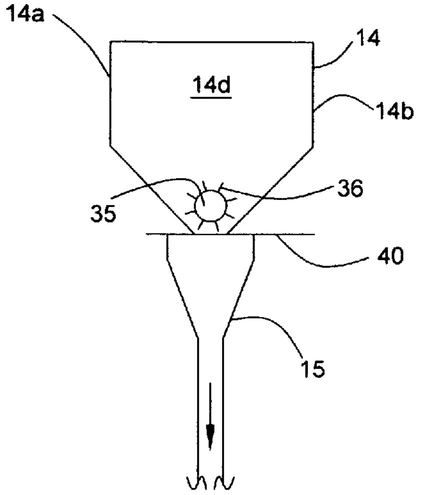
FIG. 1*b* is a partially diagrammatic cut-away side view of the feed hopper of FIG. 1*a*.
Figure 1C:
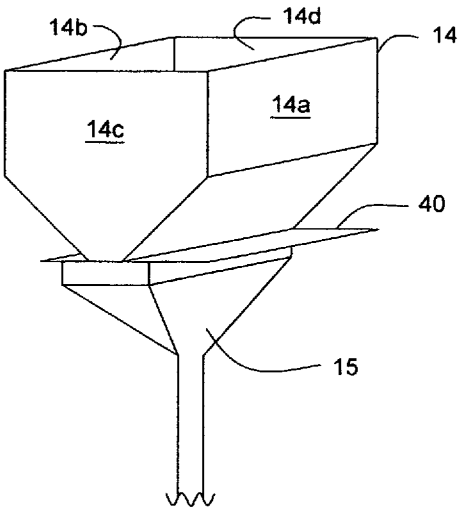
FIG. 1*c* is partially diagrammatic perspective view of the feed hopper of FIG. 1*a*.

The present invention is a method for the treatment of a canal system, that is, the treatment of the water of a canal, to remediate and counteract biological and other organic contamination therein, whereby algae and other organic debris therein is substantially destroyed, that is, decomposed or disintegrated, and whereby the canal-system water becomes substantially free of biologically-derived substances and other organic contamination which, if left intact, would foul growers' canal-water filters and/or intake screens and/or clog the canal itself, particularly where the canal water runs through underground culverts or pipes. The present method is also a device for use in carrying out the present method.

By organic or biological debris is meant herein: (a) living organisms (plant, animal or bacterium, which here are frequently but not always macro-buildups of micro-organisms); (b) the remains, vestiges and remnants of living organisms; and (c) other water-insoluble and typically-macromolecular organic matter. The terminology of organic debris, as used herein, includes algae which regularly or habitually builds up to macro-scale mats of foulant. Algae are typically aquatic, autotrophic, eukaryotic and photosynthetic organisms. Algae range from one-celled organisms to multicellular organisms such as seaweed. Algae include bladder wrack, brown alga, fungus, green alga, gulfweed, Irish moss, kelp, laminaria, phytoplankton, pond scum, red alga, rockweed, sea lettuce, sea wrack, seaweed, and tangle. Bacteria are single-celled or noncellular organisms that lack chlorophyll and reproduce by fission.

By decompose or disintegrate is meant herein to break down organic debris from a macro-scale foulant to non-fouling residues which typically are minute pieces or fragments which, particularly for instance as to algae, are no more than one or two mm. wide.

By canal or agricultural-water canal is meant herein a waterway, usually but not necessarily an artificial or constructed waterway, through which water flows from a water-storage facility (such as a reservoir) to the irrigation-water intake system of at least one agricultural grower. (A canal delivering water to a single agricultural grower would almost invariably be a private, and relatively small, canal.) These canals or agricultural-water canals are normally gravity fed and gravity driven, wherein the water is always flowing from higher to lower levels. Such canals or agricultural-water canals are typically of cement construction, although dirt canals or dirt canals lined with plastic are in use and are not excluded from the present invention. Such canals or agricultural-water canals usually, but not always, have inclined sides which, together with a flat bottom, form a blunted-V shaped profile. (The sides instead might be substantially vertical.) Such canals or agricultural-water canals typically are from about two or three feet to about sixty or seventy feet wide, and more typically from about ten to about twenty-five feet wide. Such canals or agricultural-water canals typically are from about one or two feet to about fifteen or twenty feet deep, and more typically from about five to about ten feet deep. Such canals or agricultural-water canals typically are from about one or two miles to about twenty or thirty miles long, and more typically from about five to about ten miles long. (The smaller-end widths, depths and lengths are typically seen only in private canals.)

By canal system or agricultural-water canal system is meant herein a plurality of canals fed by a single water-storage facility.

By water surface, or surface of the water, of a canal is meant herein the surface at or overlying the water within a canal. For instance, as discussed below, organic debris, particularly algae mats, at times float on the water with the canal water flowing below them, and the surfaces of such organic debris are, for the purposes of describing and defining the present invention, deemed the water surface, or surface of the water, of a canal.

The present method, particularly in preferred embodiments, successfully treats canals in an effective, economical, and environmentally-sound way. It is believed that no other known canal treatment meets all three of these criteria. The present device permits the method to be carried out effectively and economically without environmental damage.

The present method in broad embodiment includes the steps of (1) entraining biocide particles in a gaseous stream, such as an air stream, and then (2) propelling the biocide-laden (or biocide-loaded) gaseous stream (and of course the biocide entrained therein), to the water surface of the canal being treated, whereat the biocide particles are released from the gaseous stream and thereby provide a scattering of biocide particles across the water surface.

In preferred embodiments of the invention, the scattering or distribution of biocide particles is sufficiently consistent or regular. By sufficiently consistent or regular is meant that there are no significant patches of water surface that receive no biocide particles. By a significant patch of water surface is meant here an expanse having an area of $(0.1\ w)^2$ wherein "w" is the canal width. Therefore for a canal having a twenty foot width, a sufficiently consistent or regular scattering or distribution of biocide particles would leave no four-foot square area of water surface without any biocide particles.

In further preferred embodiments of the invention, the scattering of biocide particles is not only sufficiently consistent or regular but also is at least partially targeted so that in the target areas, namely those areas of water surface that are covered with floating organic debris, such as algae mats, there is no significant patch of water surface receiving more than double the amount by weight of biocide particles than any other like-size patch of water surface in or adjacent to the targeted area. Again here the term significant patch of water surface is defined as it is above.

The gaseous stream is preferably an air stream. There is currently no other known type of gaseous material that would be as hazard-free, economical and environmentally friendly as an air stream when used in the present invention. Therefore there is no practical reason to use a gaseous stream other than an air stream in the practice of the present method. For simplicity, the gaseous stream used in the method and the device of the present invention will generally be referred to below as an air stream, with the understanding explicitly being mentioned here that the present invention is not so limited, and that another type of gaseous stream may be used if one so chooses.

A liquid fluid stream or carrier is not a practical or viable alternative for a gaseous stream in the present invention (a device and method for treating canals) for a multiplicity of reasons. A chemically-inactive liquid stream in which the biocide, such as calcium hypochlorite, is to be entrained would be needed in excessively large volumes. For instance, a canal which is ten feet wide and ten miles (52,800 feet) long has a surface area of 528,000 sq. feet, and a sufficiently consistent biocide distribution would typically require covering the canal's water surface to a depth of about 0.01 feet (0.12 inches), then 5,280 cubic feet (about 39,600 gal.) of the liquid would be required. If the liquid were water, or any other liquid having a similar density, that amount of water would weigh more than one hundred fifty tons (more than 330,000 lb.). Such an enormous amount of liquid would be far too bulky and far too heavy for transporting it in the mobile unit of the present invention or in any vehicle reasonably sized for close approach to, or transport on, a canal.

Further, even the use of a water stream drawn, on-site, from the canal being treated is not a practical or viable alternative for a gaseous stream in the present device and method for treating canals. The mechanical obstacles or impediments to the use of a water stream drawn on site from the canal being treated, in combination with a land vehicle, such as the present mobile unit for example, include without limitation, (a) the one-sided weight of the in-operation ducts that would run from the canal to the mobile unit (the water intake duct), and then from the mobile unit out across the canal (the distribution duct), (b) the additional systems for pulling-in the water intake duct when by-passing obstacles along the canal being treated, and (c) the screenings and/or other filtering devices required to clean the canal water before routing it up an intake duct (to avoid fouling the entrainment and/or distribution system equipment).

Using a boat or other watercraft, rather than a land vehicle, in combination with drawing water on site from the canal is also not a practical or viable alternative because a boat sufficiently large to transport just the needed bulk of calcium hypochlorite (for instance a ton of calcium hypochlorite for a seven-mile long canal) plus one or more persons could not maneuver in a canal and could not practically be hauled out to by-pass culverts and many of the other obstacles encountered along a canal.

In addition, distribution of the biocide neat, without a fluid carrier, is also not a practical or viable alternative for a gaseous stream in the present device and method for treating canals. If the biocide was a liquid and distributed neat, for instance as a spray, it would be used at such a low level that it would be difficult, and dangerous, to apply. The danger element is introduced by the propensity of mists and other fine sprays to drift with air currents, particularly under windy conditions, and the difficulty would be the on-site creation of sufficiently fine spray or mist. The same dangers follow the impractical and unworkable broadcast of a solid biocide, such as calcium hypochlorite, wherein the dust would drift with air currents, particularly under windy conditions, and a sufficiently consistent scattering of a solid biocide by broadcasting it, in particulate form, outside of a gaseous stream would be essentially impossible.

Moreover, the postulated, and unworkable, alternatives to entraining the biocide in a gaseous stream discussed above, even if the problems they present could be overcome, would fail to provide one of the advancement and enhancements of preferred embodiments of the present device and method of treated canals, namely, embedding the calcium hypochlorite particles in the algae mats and/or other floating organic debris, whereby the calcium hypochlorite interacts with such debris from within, resulting in superior decomposition of such organic debris. It is only through the force and the speed of the air stream in which the biocide particles are entrained, and the release of the particles upon impact at the surfaces reached, that will provide the embedding of the particles within floating debris (discussed further elsewhere).

As discussed below, the biocide used in the present invention is preferably calcium hypochlorite in dry form. Further, there are no other effective biocides that are registered for the uses of the present invention other than the dry form (granules) of calcium hypochlorite described below, but should other dry forms of calcium hypochlorite, such as powders, pellets, tablets or flat flakes, or other effective "dry" biocides, such as encapsulated slow-release liquid biocides, ever become commercially-available and registered for the uses of the present invention, these other biocide particles may be used in the practice of the present invention.

The preferred biocide, calcium hypochlorite, has the chemical formula of Formula I below.

$$Ca(OCl)_2 \qquad \text{Formula I}$$

Calcium hypochlorite is also known as calcium oxychloride. It is commercially available in a dry form and it has from about 65% or 67% available chlorine. Calcium hypochlorite is a well known biocide and, more specifically, calcium hypochlorite is a well known bactericide, algaecide (algicide) and oxidizer. Calcium hypochlorite reacts with water to release chlorine and oxygen. For simplicity, the biocide used in the method and the device of the present invention will generally be referred to below as calcium hypochlorite, with the understanding explicitly being mentioned here that the present invention is not so limited, and that another type of biocide, if it is available in a suitable particle form and if it is registered for the uses of the present invention, could be employed Commercially-available calcium hypochlorite may contain a small or trace amount of cyanuric acid as a stabilizer. As a precaution against an undue or explosive reaction between calcium hypochlorite and water, water should not be added to the calcium hypochlorite, and instead the calcium hypochlorite should be added to the water, and particularly to a large amount of water. Although skin contact with, and inhalation of, calcium hypochlorite particles is a health hazard (and skin or other bodily membranes are normally moist, and thus provide the water with which calcium hypochlorite will react), calcium hypochlorite is not carcinogenic and dissipates to relatively harmless or consumed materials upon its broadcast onto the surface of a significantly large body of water in the practice of the present invention. Calcium hypochlorite has an $LD_{50}$ of 850 gm/100 kg (oral, rats).

In preferred embodiments of the present invention, the entrained calcium hypochlorite particles are not merely scattered across the water surface of a canal, but are also projected or propelled with a sufficient force so that the particles impinge the surface of the canal water. When algae mats or other organic debris are floating at or close to the water's surface, the entrained calcium hypochlorite particles do not merely impinge the surface of the canal water, they are embedded in the floating organic debris mats. In other words, the particles are surrounded by (fixed in) the mass of the organic debris, which embedment can be, and has been, visually observed. The organic debris is impregnated with the particles. The particles penetrate the surface of the organic debris and lodge for instance 0.25 or 0.5 inches under the surface.

In other preferred embodiments of the present invention, the air stream and its entrained calcium hypochlorite are not merely directed to the water's surface from a stationary position, but instead the air stream and its entrained calcium hypochlorite are ejected or discharged from a mobile unit. Such mobile unit transports the air stream's outlet, and preferably the calcium hypochlorite entrainment equipment, along at least a length of a canal so as to treat the canal water at more than a single location. In more preferred embodiments, the treatment equipment (preferably the device of the present invention) is transported along substantially the entire length of a canal whereby substantially the entire canal is treated. By substantially the entire length of a canal is meant here at least 75 percent of the length of a canal. In preferred embodiments, the canal water is treated along at least 80 or 90 percent of the length of a canal.

In other preferred embodiments, multiple concerns, including without limitation the economics, the logistics (timing and length of time of treatment), the canal's width, length and configuration, the number, sizes and shapes of obstacles along the canal, the equipment demands, the calcium hypochlorite demand of the organic debris, the variation in the calcium hypochlorite demand of the organic debris along the length of the canal, and any limitations imposed by governmental regulations, are addressed. The equipment demands include for instance: (a) the size and shape of the mobile unit; (b) the mobile unit's capability to hold and transport the solid calcium hypochlorite required for treatment of a given canal; (c) the capability of the calcium hypochlorite discharge or delivery system to both extend out across a canal and yet evade obstacles along the length of a canal; (d) the mobile unit's capacity which should provide space for an operator so that the calcium hypochlorite is safely and effectively delivered; and (e) the mobile unit's compliance with regulatory requirements such as its inside temperature for the health and safety of the workers within, and the like.

Referring now to FIG. 1 there is shown, in partially diagrammatic perspective view, a delivery system of the device of the present invention designated by the reference numeral 10. The delivery system 10 as shown in FIG. 1 includes an air blower 12, a feed hopper 14 having an associated tail member 15, and a suspended elongated tubular arm 16. The air blower 12 feeds an air stream 18 (which is shown by air-flow directional arrows 18 shown partially in phantom in FIG. 1) into the proximal end 20 of the tubular arm 16. The air stream 18 emerges from the tubular arm 16 through a plurality of ports or outlet conduits 22 along the tubular arm 16. The feed hopper 14 feeds calcium hypochlorite particles 24 (which are shown by directional-flow arrows shown in phantom in FIG. 1) to the tubular arm 16 at a point downstream from its proximal end 20 and upstream from its outlet conduits 22. In other words, the calcium hypochlorite particles 24 are fed to the tubular arm 16 at a point between the air stream 18 inlet and the air stream 18 outlet(s). The calcium hypochlorite particles 24 are taken up by the air stream 18, becoming entrained therein (facilitated by the venturi 17, which is discussed later), and exit the tubular arm 16 with the air stream 18 through the outlet conduits 22. The tubular arm 16 extends out over, and is suspended above, the water 26 (which is also shown by water-flow directional arrows 30) in a canal 28. All of the outlet conduits 22 are directed at the water 26. As shown in FIG. 1, the ports or outlet conduits 22 are short sections of open-ended pipes which are also open to the tubular arm 16, and as such provide directional control to the spray of air stream 18 and entrained calcium hypochlorite particles 24 exiting therefrom. The outlet conduits 22 preferably have discharge apertures which are adjustable in cross-sectional area (using known adjustment mechanisms) and preferably are directionally adjustable so that they can propel the calcium hypochlorite particles 24 in directions other than straight down, which is shown by alternately-positioned outlet conduits 22*a* (shown in phantom in FIG. 1) directed towards the sides of alternately-sized canal 28*a* (shown in phantom in FIG. 1).

In more detail, and still referring to FIG. 1, the air blower 12 is preferably a powered blower, such as an electric or gas-powered blower. The air blower 12 must provide a significant flow rate (unit volume per unit time). The linear velocity of the air stream 18 must be sufficient to transport or propel the entrained calcium hypochlorite particles 24 into the water 26 of the canal 28. The typical and preferred flow rates and linear velocity of the air stream 18 are approximately 1,100 standard cubic feet per minute and 150 miles per hour. Generally an air-stream flow rate within the range of from about 550 to about 1,350 cubic feet per minute, and an air-stream linear velocity of from about 40, or preferably from about 80, to about 180 miles per hour is sufficient to propel the air stream 18 and its entrained calcium hypochlorite particles 24 into the water 26 of the canal 28 with sufficient force to embed the calcium hypochlorite particles 24 in any floating mats of organic debris (not shown in FIG. 1).

The linear velocity of the air stream as it leaves the outlet(s) of a delivery system of the present invention (which are, as shown in FIG. 1, the outlet conduits 22 of the tubular arm 16) should in preferred embodiments be sufficient to propel the air stream and its entrained calcium hypochlorite particles into the water of a canal with sufficient force to embed entrained calcium hypochlorite particles in any floating mats of organic debris in water. The air flow rate depends on many factors. The output of the blower primarily determines the linear velocity and the air flow rate (volume per unit time) but these factors are impacted by the length of the delivery tube, diameter of the delivery tube, number of openings directed over the canal and orifice size of each opening directed over the canal. In practice, once these parameters are set for a particular canal, the factors that are varied as the mobile unit advances along the length of the canal are (a) the amount of calcium hypochlorite that is fed into the air steam and (b) the speed of the mobile unit which also impacts the dosage level delivered to the water surface.

Now referring again to FIG. 1, and also to FIG. 1*a*, FIG. 1*b*, FIG. 1*c* and FIG. 1*d*, which are respectively cut-away front and side views, and perspective view, of the feed hopper 14 and its tail member 15 (FIG. 1*a*, FIG. 1*b* and FIG. 1*c*) and the venturi system 17 within the tubular arm 16, it is seen that the feed hopper 14 in this embodiment has a tapering side-view profile. Its front or first wall 14*a* and its rear or second wall 14*b* are parallel to each other in their upper regions and then bend or taper to become oppositely inclined from vertical and approach, but do not meet, each other near the bottom of the feed hopper 14. The side walls 14*c* and 14*d* are pentagonal and parallel each other. The feed hopper 14 contains the calcium hypochlorite particles 24 that are being fed into the tubular arm 16, which is part of the blower system of the delivery system 10. Preferably the calcium hypochlorite particles 24 are fed into the tubular arm 16 at a specific rate (delivery rate) to provide a target concentration of calcium hypochlorite particles 24 in the air stream 18, and therefore the calcium hypochlorite feed rate preferably is dependent on the flow rate and linear velocity of the air stream 18 at the time the calcium hypochlorite particles 24 are fed to the air stream 18. The maintenance of a supply of calcium hypochlorite in the feed hopper 14 in the embodiment shown in FIG. 1 may be done manually maintained, for instance by filling the feed hopper 14 from fifty or hundred pound pails.

As with all granular solids in a pail or other like open device, the solid calcium hypochlorite sometimes forms clumps. These clumps preferably should be broken up because if they are not, they typically are too large (generally larger than 1 mm) for feeding properly to the tubular arm 16 and would typically plug the venturi system (venturi 17) in the tubular arm 16. In general, when the feed of calcium hypochlorite particles to the blower system has a reasonably uniform particle size distribution, that factor facilitates a uniform delivery of the calcium hypochlorite particles to the water of a canal. The calcium hypochlorite particles therefore preferably should have a reasonably uniform particle size, and preferably should be a fine solid or dust, because such characteristics facilitate the take-up of the calcium hypochlorite into the air stream. Further, if the calcium hypochlorite particles, which as commercially-supplied have a particle size distribution of from 1 mm, or less than about 1 mm, to a fine dust of about 0.1 mm, are ground even finer, a narrower and more uniform particle size distribution is provided. Calcium hypochlorite particles having a narrower and more uniform particle size distribution are distributed more uniformly in the air stream and are driven more uniformly into organic debris masses. Generally in the practice of the present invention, bottom-hopper grinding or pulverization, just ahead of feeding the calcium hypochlorite to the air stream, is preferred.

Such bottom-hopper grinding is accomplished in the delivery system 10 shown in FIG. 1 by a rotating shaft or spindle 35 at or near the bottom of the feed hopper 14. That spindle 35 runs the entire width of the hopper 14, and as best seen in the side view of FIG. 1*b*, fits closely between the hopper's front and rear walls 14*a*, 14*b* where they most closely approach each other. The spindle 35 has many stainless steel spokes or tines 36 radiating outwardly. The spindle 35 is operationally associated with a high torque motor 38 which rotates the spindle 35 about its axis.

Directly below the spindle 35 is an adjustment plate 40 which is translatable between a closed position whereat it completely closes off the hopper 14 (at its bottom orifice 32) from the tail member 15 to a fully open position whereat the hopper 14 is at its maximum openness to the tail member 15, and to any desired position in between the completely-closed and the fully open positions. When the adjustment plate 40 is in at least partially open position, the calcium hypochlorite particles 24 in the hopper 14 are gravity-fed downwardly, flowing down past the spindle 35 into the tail member 15. As the calcium hypochlorite particles 24 pass the motor-driven spindle 35, its tines 36 grind the particles 24 to finer particle sizes having a narrower and more uniform particle size range that will provide a better matrix for treatment when entrained in the air stream 18, as discussed above.

To commence the feeding of the calcium hypochlorite particles 24 to the air stream, the normally-closed orifice 32 in the feed hopper 14 is opened and/or the size of the orifice 32 is adjusted to obtain the desired delivery rate by a translation of the adjustment plate 40. To assure that the orifice 32 does not become clogged with calcium hypochlorite particles 24, the spindle 35 and its tines 36 rotate or spin in the bottom of the hopper 14, just upstream of the orifice 32. Besides preventing clogging of the orifice 32 and facilitating a controlled delivery of the calcium hypochlorite particles 24 to the tubular arm 16, the spinning spindle 35 grinds and pulverizes the calcium hypochlorite particles 24, breaking up clumps, and thereby feeding the calcium hypochlorite particles 24 as a stream having a more uniform particle size distribution than is typical for calcium hypochlorite as it is commercially supplied, as discussed above.

Figure 1D:
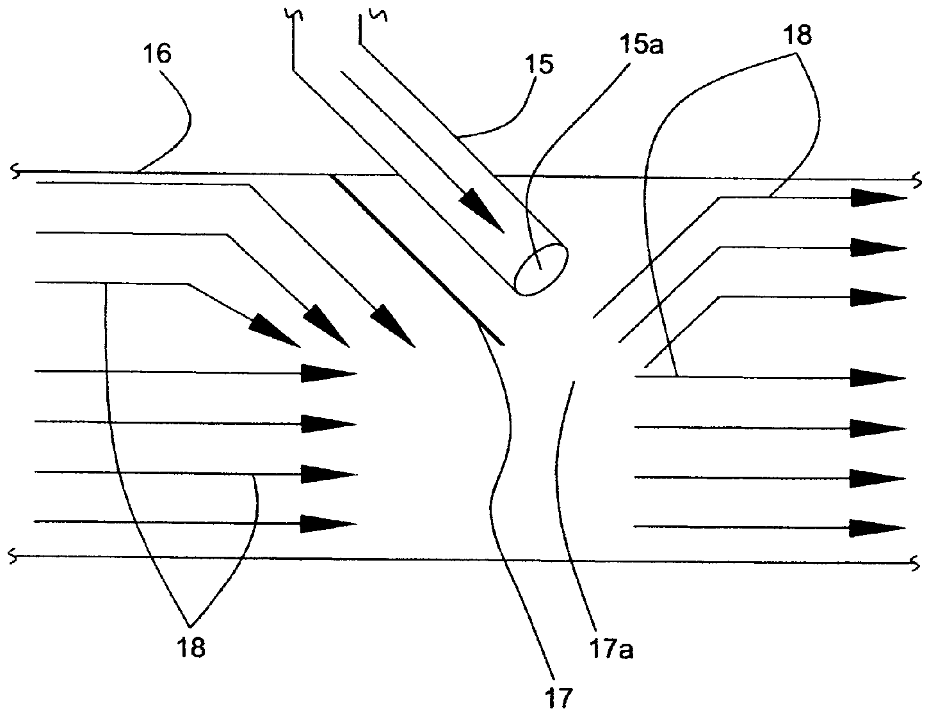
FIG. 1*d* is a diagrammatic and enlarged view of a venturi system of the delivery system shown in FIG. 1.

Referring again to the delivery system 10 of FIG. 1, an eductor or venturi (venturi system) 17 (shown diagrammatically in FIG. 1 and FIG. 1*d*) is utilized to transport the calcium hypochlorite particles 24 into the rapidly-flowing air stream 18. The tail member 15 enters the tubular arm 16 at the venturi system, just downstream of the venturi 17 which forces the air stream 18 into a narrower stream just below the point where the tail member 15 discharges calcium hypochlorite particles 24, which have passed downwardly from the feed hopper 14, when its bottom orifice 32 is at least partially open, into the tail member 15. The venturi 17 is disposed within the tubular arm 16 as shown in FIG. 1*d*, and is comprised of a downstream-tilted baffle which channels the air stream around it, namely to that area of the tubular arm 16 not blocked by the venturi 17. As shown and in preferred embodiments, the tail piece 15 is also downstream-tilted as it enters the tubular arm 16 and is disposed within the shadow of the venturi 17. Relative to the flow of the air stream 18, the restricted or narrowed air flow region 17*a* is below the discharge orifice 15*a* of the tail piece 15, so that the discharge is to the region of air flow 18 just at the point where it begins to expand back to the full cross-sectional area of the tubular arm 16. The air stream 18 is traveling at a fast speed, for instance in the range of 80 to 180 mph, as it speeds through the tubular arm 16. In the restricted air flow region 17*a* the air stream 18 will compress and increase speed. Behind the venturi 17 the venturi effect produces a negative pressure, i.e., an air pressure that is less than atmospheric pressure, at the discharge orifice 15*a* of the tail member 15 which sucks or draws down the calcium hypochlorite particles 24 directly into that part of the air stream 18 which is streaming past the discharge orifice 15*a*. Therefore the air stream 18 will at least initially be calcium-hypochlorite-laden in its core or center, and not about its periphery which additionally facilitates keeping the calcium hypochlorite particles 24 entrained until the air stream 18 hits the target surface(s) at which the calcium hypochlorite particles 24 are released and the air stream 18 dissipates to atmosphere.

As shown diagrammatically in FIG. 1, the calcium hypochlorite-laden air stream 18 (and the air stream 18*a* being discharged by angled outlet conduits 22*a*) is propelled down to the water 26 of the canal 28 from the outlet conduits 22 of the tubular arm 16. The tubular arm 16, as shown in FIG. 1 and generally, is suspended above the water 26 and substantially spans the width of the canal 28. (Canals typically range from about eight to about twenty feet in width.) The outlet conduits 22 along the tubular arm 16 are relatively short tubes that are open to the tubular arm 16 at their proximal ends and are open at their distal ends. The outlet conduits 22 are the discharge openings for the calcium hypochlorite-laden air stream 18. The outlet conduits 22 are preferably short passageways as shown rather than mere orifices in the tubular arm 16 for several reasons including the capability of being separately set at angles other than straight down, as shown in phantom as outlet conduits 22*a* discharging air streams 18*a*. This is particularly advantageous if it is desirable to angle the closest or farthest outlet conduit 22 towards the water 26 closely adjacent to the side of the canal 28, which in FIG. 1 is shown alternatively via the angled outlet conduits 22*a* directed to the sides of the wider canal 28*a*. The conduit outlets 22 preferably can also be all (or separately) adjusted in length to decrease the distance between the open ends of the conduit outlets 22 and the target canal water 26. The surface of the water 26 preferably should be covered with a sufficiently consistent amount of calcium hypochlorite particles 24 although the operator, by varying the amount of calcium hypochlorite particles 24 being fed to the air stream 18 per unit time, can adjust the dosage of calcium hypochlorite particles 24 being delivered at different sections along the length of the canal 28 usually in accordance with the amount of organic debris per unit area or per unit volume of water. In other words, the calcium hypochlorite dosage delivered preferably is in proportion to the degree of biological remediation required. Examples of mobile equipment which can be used to suspend the tubular arm 16 above the canal 28, substantially spanning its width, are described below.

Since solid calcium hypochlorite is extremely corrosive, the various components of the present delivery system that come into contact with it, even transitorily or fleetingly, such as air blower 12, the feed hopper 14 and the tubular arm 16 of the delivery system 10 of FIG. 1, and the venturi 17 in the tubular arm 16 (shown best in FIG. 1*d*), preferably are constructed from corrosion-resistant materials such as polyethylene, polypropylene, polycarbonate and polyvinyl chloride, or are metallic components coated or covered with corrosion-resistant materials such as these, or the like.

To treat the entire length of a canal (an entire canal), the calcium hypochlorite and the delivery system must be transported or conveyed along the many miles of the canal's length, and the delivery rate of the calcium hypochlorite must be adjusted according to the degree of biological remediation required for the various sections along the canal. By "degree of biological remediation" is meant herein the amount of organic debris requiring treatment per unit surface area. For instance, algae levels typically will vary dramatically along the length of a canal and the present invention's calcium hypochlorite addition rates preferably are adjusted repetitively, or at times almost constantly, so that a sufficiently consistent, and an appropriate or biologically-remedial, amount of calcium hypochlorite is delivered to the surface of the canal water. By a "biologically-remedial amount of calcium hypochlorite" is meant herein an amount of calcium hypochlorite per unit surface area sufficient to decompose or disintegrate the organic debris on a macro scale. The canal water is preferably not being purified on a micro scale. A micro-scale purification is not need for the purposes of the present invention, which is to clear up organic-debris choked canals. Instead it is sufficient that the canals are visibly free of organic debris, or at least have visibly less organic debris, within twelve hours after treatment in comparison to the canal's condition before treatment, and remain in a better-than-before-treatment condition for at least eight days. Further, essentially all canals will continue to be inoculated with microbiologicals because they are open to atmosphere and to other sources of organic-debris contamination and therefore they will be subjected to post-treatment organic-debris buildup. Given the inevitable post-treatment organic-debris buildup, it would be impractical, wasteful, unnecessarily costly and environmentally unsound to treat a canal with more than a biologically-remedial amount of calcium hypochlorite.

Transportation or conveyance of the calcium hypochlorite and the delivery system along a canal is, as mentioned above, provided by a mobile unit, that is, a land-transport vehicle, including without limitation a truck, a trailer or other automotive vehicle. In preferred embodiments of the present invention as now envisioned, the output of the present delivery-system is determined and controlled by at least one operator. Such an operator typically would ride in, or drive, the mobile unit. Such an operator typically would also be repetitively or constantly determining the degree of biological remediation required for the at-hand or upcoming canal section, and determining the calcium hypochlorite addition rate that is adequate or appropriate to meet it. In other words, such an operator must both repetitively or constantly determine the dosage (amount of calcium hypochlorite required per unit water-surface area) based on an analysis of the organic debris levels and adjust the calcium hypochlorite feed rate appropriate to deliver the required dosage. The mobile unit typically would be traveling along the canal being treated at speeds of from about two to ten miles per hour. Low speeds in such a range usually provide the operator a sufficient amount of time to perform these tasks in a timely manner.

In more detail, in preferred embodiment, as the equipment (mobile unit equipped for calcium hypochlorite delivery) travels down a canal, the operator visually observes both the canal-water flow rate and degree of biological loading (organic debris loading) along the canal. The operator then adjusts or regulates the calcium hypochlorite dosage being delivered by two methods, which can be and not uncommonly are both employed, either concurrently, consecutively or sequentially. The first is an adjustment to the amount of calcium hypochlorite that is added to the air stream. When heavier biological loading is seen in the canal, more calcium hypochlorite is added to the air stream. This is accomplished by opening or closing the delivery or adjustment plate (such as the adjustment plate 40 shown in FIG. 1*b* above) contained in the grinding orifice or region at the bottom of the feed hopper. The second method for adjusting the calcium hypochlorite dosage being delivered is the speed at which the mobile unit is traveling down the canal. When a change in the degree of biological loading (organic debris loading) in the canal is encountered, changing the speed of the mobile unit alone will change the level of calcium hypochlorite that is being delivered to the canal per unit surface area. Slowing the mobile unit increases the calcium hypochlorite being delivered, and increasing the speed of the mobile unit decreases the calcium hypochlorite being delivered. When a driver and operator are both in the mobile unit, the change-of-speed deliver adjustment is accomplished by the operator instructing the driver to speed up or slow down, typically via a communication system between the driver and operator since they usually would be physically separated.

The interplay or interchange between calcium hypochlorite-dosage adjustment or regulation methods is usually set by the practicalities of the circumstances or conditions. As noted above, preferably the mobile unit travels within the range of two to ten miles per hour, and therefore the calcium hypochlorite-regulation demands obviously can exceed the adjustments possible via mobile-unit speed.

Under present governmental regulations, there are many conditions and restraints governing vehicles used for the purposes, and in the environment, of the present invention. These conditions and restraints concern the mobile unit and its operator and stem primarily from the regulations concerning the handling and distribution or dispersal of calcium hypochlorite. In preferred embodiments of the present device, as generally noted elsewhere herein, an operator is constantly present and actively handling the calcium hypochlorite delivery, including adjusting the calcium hypochlorite/air feed ratio, instructing the driver regarding the desired mobile-unit speed, raising and lowering the boom (discussed below) and keeping the feed hopper full (manually by bucketing or otherwise transferring calcium hypochlorite into the hopper). For health and safety reasons related to the operator, the operator must wear the proper safety equipment, particularly including a respirator, sealed goggles, chemical resistant gloves, protective apparel such as work wear protective of dry-particulate hazards available under the Tyvek® trademark (Tyvek® is a registered trademark of E. I. DuPont Nemours & Co. of Wilmington, Del.) whenever the operator might be exposed to the calcium hypochlorite, air born or otherwise. Similarly there are inside-temperature restrictions applicable to the mobile unit, and therefore the mobile unit must be equipped with sufficient heat and/or air conditioning controls to provide the required inside temperatures. In addition, for practical reasons, when the assessment of the degree of organic debris requiring remediation is being done visually (by visual inspection) while the mobile unit is moving, glass, polycarbonate or other chemically-resistant windows from which the canal can be seen must be available to the operator.

Figure 2:
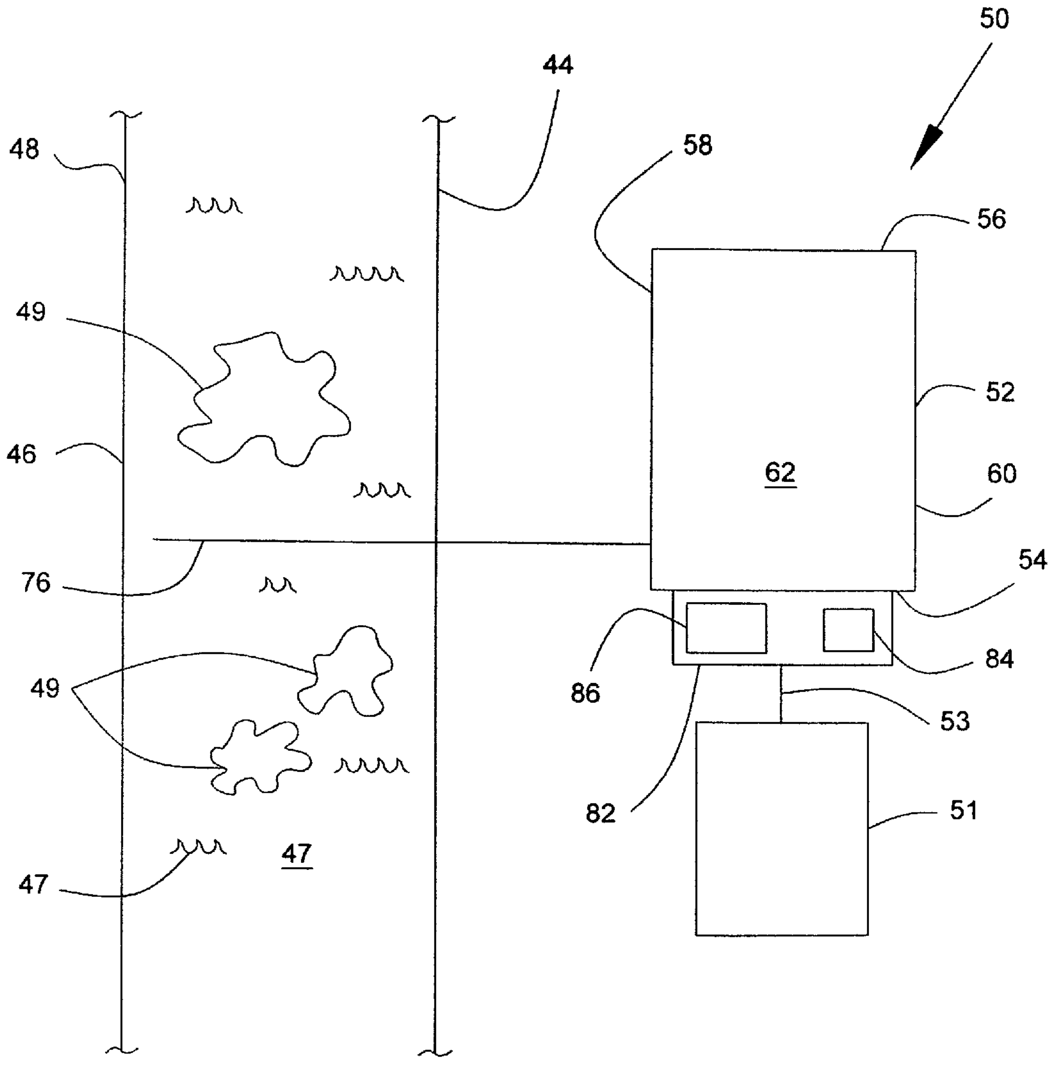
FIG. 2 is a partially diagrammatic view of a mobile unit of the present invention positioned on the side of a canal with its boom extending sideway across the canal.
Figure 3:
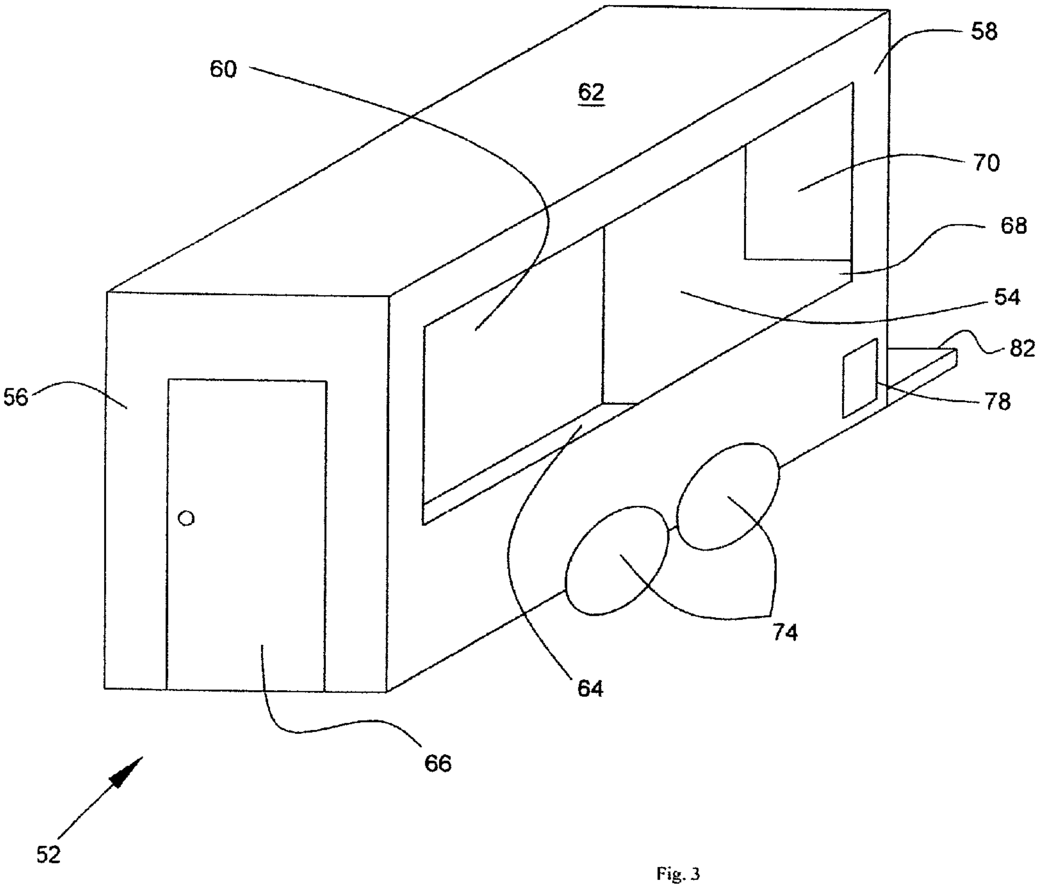
FIG. 3 is a partially diagrammatic view of a mobile unit of the present invention.

Referring now to FIG. 2 and FIG. 3, there is shown an embodiment of a mobile unit 50, which is an element of a mobilized delivery system of the present invention. In this embodiment, the mobile unit 50 as shown is a combination of a truck 51 and a self-contained and enclosed trailer 52. The trailer 52 alone is shown in FIG. 3, and the truck 51 and trailer 52 plus a towing hitch 53 interconnecting them are shown in FIG. 2. The truck 51 is shown towing the trailer 52 along the near side 44 of a canal 48.

Referring in particular to the details of the trailer 52 as shown in FIG. 2 and FIG. 3, the trailer 52 has a front wall 54 and an opposed rear wall 56, a first side wall 58 and an opposed second side wall 60, a top wall 62 and an opposed bottom wall 64. The rear wall 56 holds a door 66 for entry into, and exit from, the trailer 52. The first side wall 58 has an expansive viewing window 68 and a small second viewing window 70 is located in the front wall 54, and there is a small port (not shown) on which is mounted an air conditioning unit (not shown). The viewing window 68 and the second viewing window 70 are preferably formed of a transparent material such as Plexiglas® plastic sheets (Plexiglas® is a registered trademark of Arkema France, a French corporation of Colombes, France) or other glass substitute. The viewing windows 68, 70 may instead be formed of glass, such as automotive window glass, but glass generally is less practical than glass substitutes because the viewing openings can be very large, for instance forty by sixty inches, and the jarring when ruts and the like are encountered along a canal can shatter glass. The viewing window 68 and the second viewing window 70 must be transparent (easily seen through) so that the canal 48 and any organic debris 49 (shown in FIG. 2) floating on the surface of the water 47 of the canal 48 can be clearly seen by an operator who is inside of the trailer 52. The trailer 52 is of course mounted on wheels, such as a conventional set of four trailer wheels 74 (of which only the wheels 74 on the first side wall 58 are shown in FIG. 3). Also shown in FIG. 2 and FIG. 3 is a platform 82 on which is mounted blower 84 for generating an air stream (not shown). Such air stream is routed to a delivery system by conventional conduits (not shown). Also shown mounted on the platform 82 in FIG. 2 is a generator 86, the purpose of which is described blow.

The trailer 52 shown in FIG. 2 and FIG. 3 is the operational hub of the mobile unit 50, or mobile-unit hub. In other words, the trailer 52 shown in FIG. 2 and FIG. 3 is the operational (activity and equipment) center of a vehicular unit that is equipped for the safe delivery of calcium hypochlorite particles to the water of a canal, along the length of the canal, such as the water 47 of the canal 48 shown in FIG. 2. The trailer 52 as shown is, however, not itself mobile, and must be transported along the length of the canal 48, such as by being towed or pulled along by the truck 51 as shown in FIG. 2. The trailer 52 as shown is constructed from strong yet reasonably light-weight materials such as carbon-steel and sheet material, and it usually is larger than a conventional road vehicle. A trailer such as trailer 52 would have double axles and would be large enough to transport on the order of 1000 pounds of calcium hypochlorite. The truck, such as the truck 51 shown in FIG. 2, also typically holds about 1000 pounds of calcium hypochlorite. The calcium hypochlorite is typically commercially-supplied in 50 or 100 pound sealed pails, and preferably it is kept in such sealed pails for safety in handling and accounting (dosage level) during a canal treatment process until, of course, a pail is opened and its contents are loaded to the feed hopper (not shown in FIG. 2).

The trailer 52 shown in FIG. 2 and FIG. 3 is about ten feet long, seven feet wide and seven feet high, or in other words it has an internal volume or capacity of about 490 cubic feet. In preferred embodiments of the present invention, the mobile-unit hub has an internal volume or capacity of from about 300 to about 700 cubic feet, and more preferably from about 400 to about 600 cubic feet. Mobile-unit hubs smaller than this are typically impractically small and mobile-unit hubs larger than this are typically impractically and unnecessarily large because they provide unneeded internal capacity while their greater bulk complicates their handling and can impede their mobility, unless of course other demands and/or concerns call for such smaller or larger mobile-unit hubs. A smaller trailer with less calcium hypochlorite storage space and a shorter boom could used for smaller canals. Similarly, a larger trailer could be used for larger canals provided there was enough space to move the trailer or other vehicle along the canal. Most roadways along the canal are very tiny and have multiple bends making it impossible for large vehicles system to drive down the canals.

Alternative mobile-unit approaches include without limitation suitable integrated or unified mobile units such as a flatbed truck having a shell mounted on the normally flat and open-side section behind the driver's cabin to form the mobile-unit hub and an oversized van in which the mobile-unit hub is disposed behind the driver's seat.

The mobile unit of the present invention generally requires a suspension system to keep the tubular arm of the delivery system, that it, the pipe through which the air stream with its entrained calcium hypochlorite travels, properly oriented over the canal that is being treated. This suspension system may be comprised of a suspension arm or boom that is attached to the mobile unit and that is supported/controlled by a pulley system. The suspension system facilitates the delivery of a uniform amount of calcium hypochlorite particles. The suspension arm or boom is preferably constructed from a light-weight metal such as aluminum or other light-weight material such as a polymeric composite. The arm or boom preferably is variable in length and preferably can be raised and lowered during the treatment process. The variable-length feature is routinely demanded by the variable widths of the canals which are targeted for treatment. The vertical displacement feature, i.e., the raising and lowering, is routinely demanded by the diverse obstacles that are typically encountered along the canals that would otherwise collide with the boom or approach colliding with the boom. These diverse obstacles include without limitation irrigation valves, growers' pumping and filtration stations, signs, antennae, fertilizer tanks, filtration and power structures of the canals, and road crossings. Such suspension systems are discussed below in conjunction with their depictions, in whole and in part, in the drawings.

The trailer 52 as shown in FIG. 2 is equipped with a boom 76 which is an elongated and extendable pole or arm. For simplicity only an empty boom mount or socket 78 is shown in FIG. 3. As best illustrated in the diagrammatic FIG. 2, the boom 76 is mounted on the first side wall 58 of the trailer 52, and in its extended posture or position the boom 76 runs from the first side wall 58 of the trailer 52 out and over the canal 48. As shown in FIG. 2, and in preferred embodiments of the present invention, the boom 76 extends to a sufficient length so as to reach, or approach reaching, the far side 46 of the canal 48. In other words, when the trailer 52 is running along the near side 44 of the canal 48, and parallel to the length of the canal 48, the boom 76 projects out sidewards from the trailer 52 substantially perpendicular to the length of the canal 48 and extends: (a) across the gap between the trailer 52 and the near side 44 of the canal 48; (b) across the near side 44 of the canal 48; and (c) substantially across the water 47. The purpose of the boom 76 is to support the calcium hypochlorite delivery system (such as the delivery system 10 shown in FIG. 1 discussed above) as discussed in more detail elsewhere.

Figure 4:
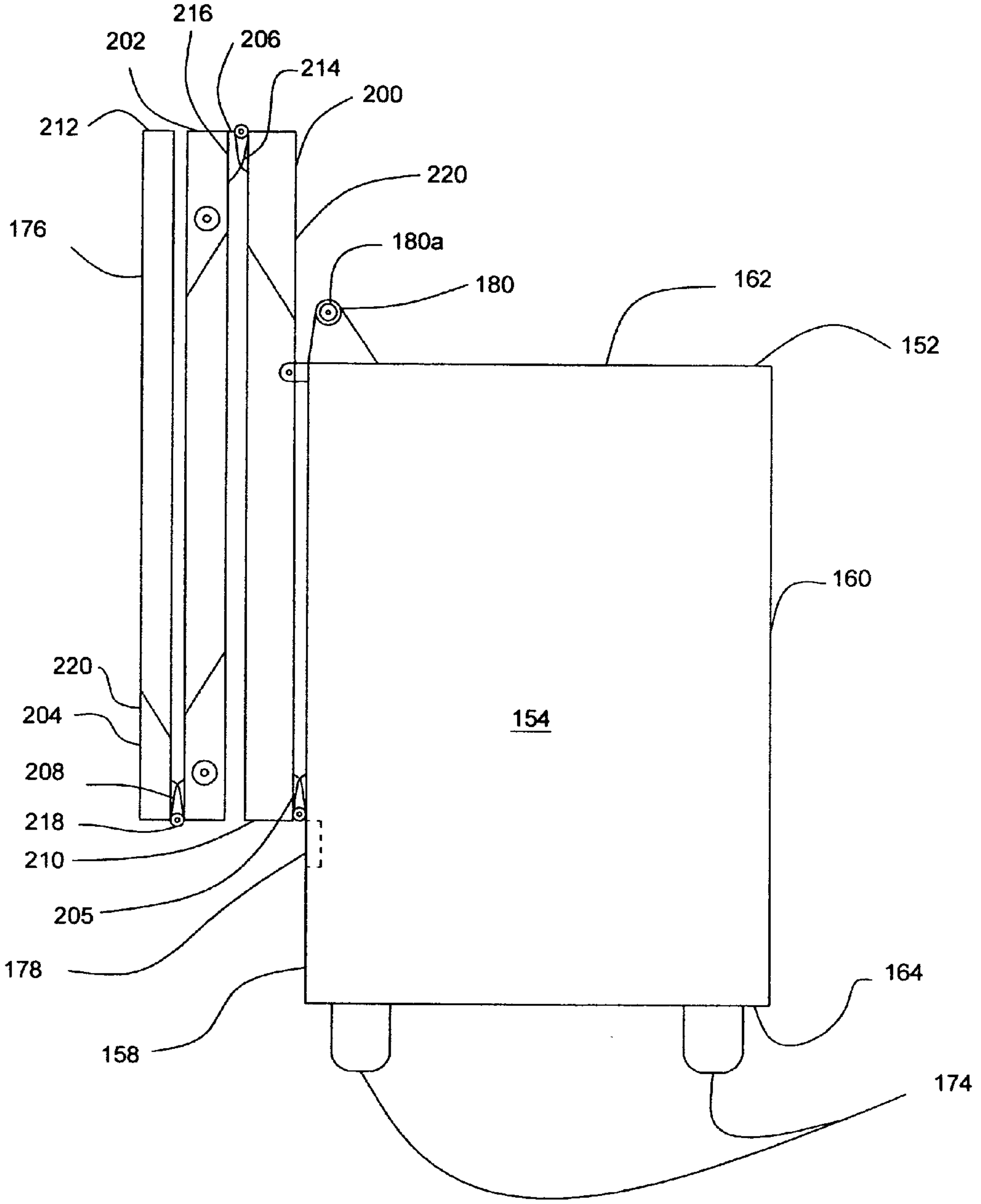
FIG. 4 is a partially diagrammatic view of a mobile unit of the present invention shown with a boom in a position retracted against the side of the mobile unit.
Figure 5:
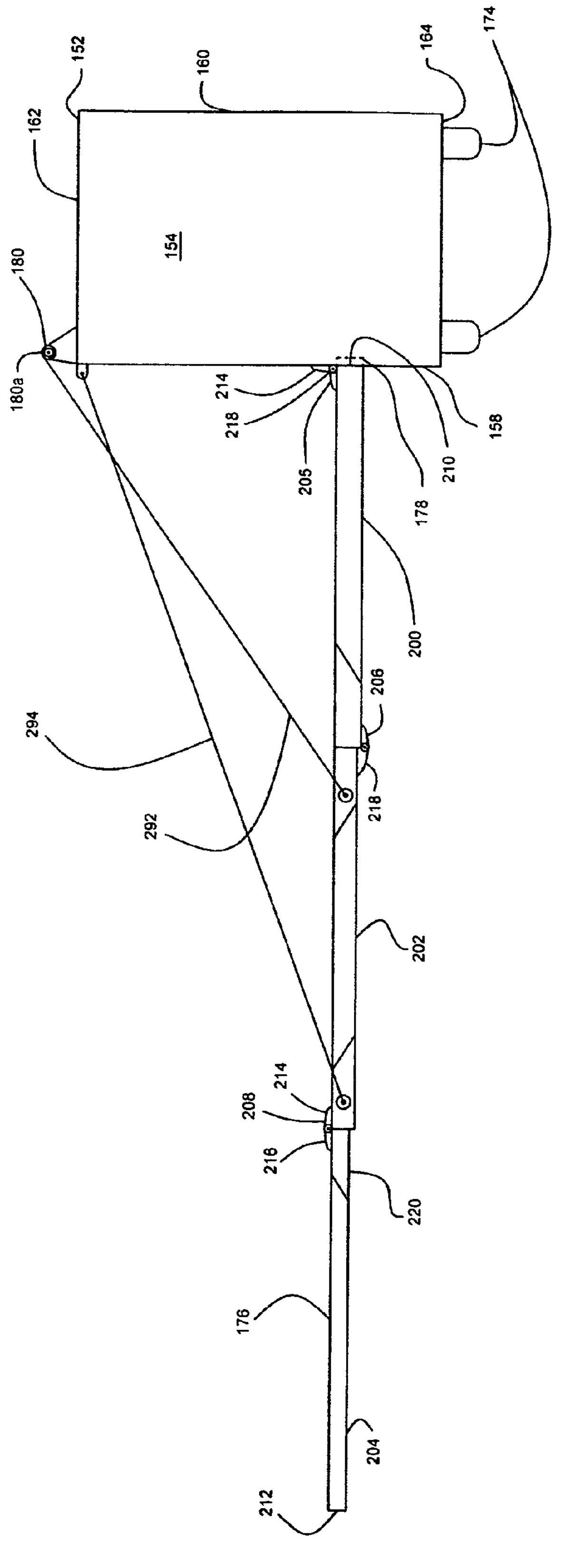
FIG. 5 is a partially diagrammatic view of a boom and mobile unit of FIG. 4, shown with the boom in a position extended sideward over the canal.

Referring now to FIG. 4 and FIG. 5, there is shown (partially diagrammatically) a trailer 152 having a front wall 154 (without any platform, for simplicity), a rear wall (which is not shown in either FIG. 4 or FIG. 5), a first side wall 158, a second side wall 160, a top wall 162, a bottom wall 164, a boom socket 178 (shown in phantom because it is disposed rearward of the forward wall 154), a boom 176, wheels 174 and a pulley 180 mounted on the trailer 152 along the top wall 162. The boom 176 is articulated, and the articulation shown in FIG. 4 and FIG. 5 is a three-section, two-joint articulation. In other words, the boom 176 is comprised of three elongated segments, namely a near or proximal segment 200, a middle segment 202 and a distal segment 204. The proximal segment 200 and middle segment 202 are coupled or end-to-end connected at a first joint 206. The middle segment 202 and distal segment 204 are coupled or end-to-end connected at a second joint 208. As shown, and in preferred embodiments, the boom 176 segments, that is, the proximal segment 200, the middle segment 202 and the distal segment 204, are each about eight feet long, and in combination they comprise a boom (here, the boom 176) which stretches out sideward about twenty-four feet, running from the boom socket 178 on the trailer 152 across the gap between the trailer 152 and a canal, and across a canal (not shown in FIG. 4 or FIG. 5) to the canal's far side such as is depicted in FIG. 2 discussed above.

The boom 176 has a proximal end 210 and a distal end 212. The boom 176 is shown folded up accordion-style against the first side wall 158 of the trailer 152 with its proximal end 210 shown not seated in, but instead adjacent or slightly spaced-apart from and above, the boom socket 178 in FIG. 4. The boom 176 is shown unfolded or extended sideward, substantially along the horizontal, with its proximal segment 200 seated in the boom socket 178 in FIG. 5. When the boom 176 is folded up against the first side wall 158 of the trailer 152: (a) the proximal segment 200 runs upward along or substantially parallel to the first side wall 158 of the trailer 152 and somewhat beyond the first side wall 158, past the top wall 162; (b) the middle segment 202 runs back downwardly alongside of the proximal segment 200; and (c) the distal segment 204 runs back upwardly alongside of the middle segment 202. When the boom 176 is unfolded or extended, the proximal segment 200, middle segment 202 and distal segment 204 are arranged or disposed end-to-end along the horizontal and are held up or supported in that position by a pair of lines or stays 292, 294 which run from opposed ends of the middle segment 202 up to the pulley 180 as discussed below. Variations in lengths of boom segments, and the reach that should preferably be provided by a boom, generally are discussed elsewhere herein.

In addition to the first joint 206 and second joint 208 connecting respectively the proximal segment 200 and middle segment 202, and middle segment 202 and distal segment 204, there is an inner joint 205 connecting the boom 176, or more specifically the proximal segment 200 of the boom 176, to the trailer 152, or more specifically the first side wall 158 of the trailer 152. Each of these joints is operably comprised of a winged or leafed hinge 214 translatable from a folded position in which the leaves 216 are aligned side-by-side as seen in FIG. 4 to an open position in which the two leaves 216 are spaced-apart and lie on opposite sides of the pivot-point barrel 218 of the hinge 214 as seen in FIG. 5. In more detail, the hinge 214 of the inner joint 205 straddles the first side wall 158 of the trailer 152 and the upper surface of the proximal segment 200 of the boom 176 (upper surface when the boom 176 is extended), and is translatable from a closed position, as seen in FIG. 4, to a 90-degree open position, as seen in FIG. 5. The hinge 214 of first joint 206 straddles the lower surfaces of the proximal segment 200 and the middle segment 202 of the boom 176 (lower surfaces when the boom 176 is extended sideward), and is translatable from a closed position, as seen in FIG. 4, to a 180-degree open position as seen in FIG. 5. The hinge 214 of second joint 208 straddles the upper surfaces of the middle segment 202 and the distal segment 204 of the boom 176 (upper surface when the boom 176 is extended sideward), and is translatable from a closed position, as seen in FIG. 4, to a 180-degree open position as seen in FIG. 5. The leaves 216 are each secured substantially flat to the component on which it is mounted by conventional mechanical fasteners. The leaves 216 of the hinge 214 of first joint 206 and the hinge 214 of the second joint 208 are secured to sleeves 220 which cover the adjacent ends of the middle segment 202 and distal segment 204 to which the hinges 214 are secured. Such sleeves 220 are provided to strengthen the middle segment 202 and distal segment 204 at the region of the first joint 206 and second joint 208. The sleeves 220 can be carbon steel tubes or other strong material. When in their open positions, the hinges 214 are each separately locked into place with a removable pin (not shown) which is inserted in the barrel 218, whereby the leaves 216 of the hinges 214, and particularly the hinges 214 of first joint 206 and second joint 208, are unable to move beyond the 180-degree open positions.

When extended, the boom 176 is suspended in its normally-horizontal position over a canal by a cable 292 which runs from pulley 180 down to the sleeve 220 of middle segment 202 at first joint 206. When an obstacle is encountered in a canal as the trailer 152 is traveling along such canal, the boom 176 can be lifted out of the way, pivoting at the boom socket 178, by retracting the cable 292, which runs over a grooved wheel 180*a* of the pulley 180 and is retracted with a motorized winch (not shown) mounted inside of the trailer 152. Collisions between the boom 176 and obstacles in a canal are thus avoided without releasing the locked hinges 214 or folding the boom 176. A second cable, namely a dampening cable 294, runs from a position close to the pulley 180 to the sleeve 220 of the middle segment 202 at the second joint 208 and is provided not for the purpose of suspending the boom 176 over a canal but instead for the purpose of dampening vibrations along the boom 176 and thereby holding the boom 176 in the desired sideward position.

In preferred embodiments, and as it is shown in FIG. 4 and FIG. 5, the boom 176 is translated to and from its folded-up or stored or collapsed mode against the first side wall 158 of the trailer 152 manually, and it can be secured in its collapsed mode by straps or other suitable mechanical fastener(s). In its folded-up or stored or collapsed mode, which is shown in FIG. 4, the boom 176 projects out only slightly above, and slightly to the side of, the trailer 152, and thus the trailer 152 is reasonably unhindered by the boom 176 as it is moved from site to site.

A boom such as the boom 176 need not have eight-foot segments, nor three segments, as shown (the proximal segment 200, middle segment 202 and distal segment 204 which unfold to a twenty-four foot length). A boom such as the boom 176 could instead be comprised of two eight-foot segments and span a distance of about sixteen feet when unfolded, or three six-foot segments and span a distance of about eighteen feet when unfolded, or two eight-foot and one four-foot segments and span a distance of about twenty feet when unfolded. A boom such as the boom 176 could be comprised of four seven-foot segments and span a distance of about twenty-eight feet when unfolded, or a combination of an eight-foot and two five-foot segments and span a distance of about eighteen feet when unfolded. (The segments 200, 202 and 204 as shown, and in preferred embodiments, are obviously detachable and interchangeable.) The lengths of the boom segments, such as the proximal segment 200, middle segment 202 and distal segment 204 of the boom 176 of FIG. 4 and FIG. 5, whether the lengths are the same or different, are variable features and should preferably be sufficient in combination to provide, when unfolded and extended, an effective horizontal length (length along the horizontal) which extends from the boom socket 178 out over a canal being treated, and terminating at a point sufficiently close to the far side of the canal being treated. A point sufficiently close to the far side of a canal being treated generally is a point that is no more than one-tenth of the canal width away from the far side of a canal as measured along the horizontal.

Figure 6:
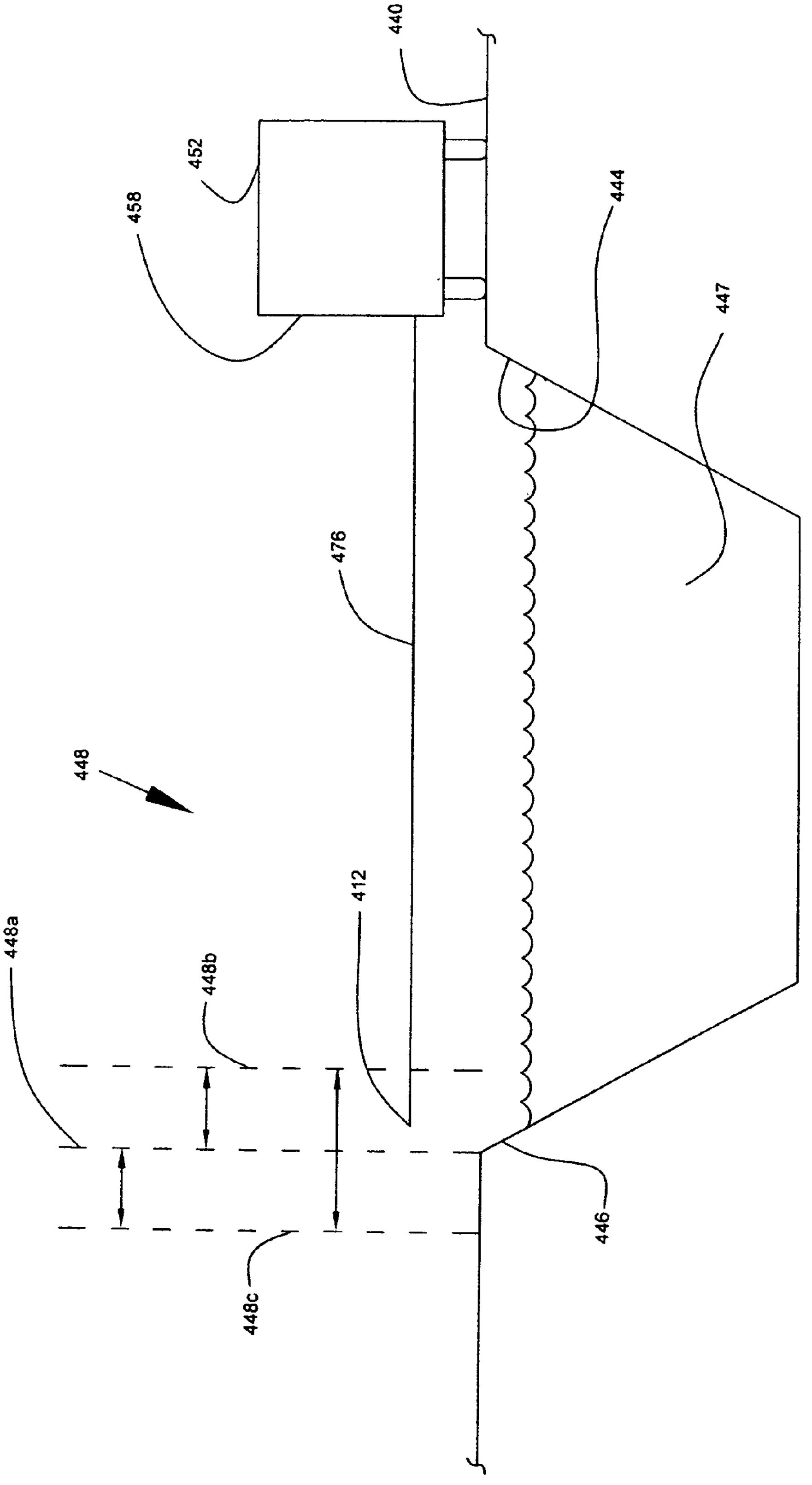
FIG. 6 is a partially diagrammatic view of the mobile unit of the present invention shown with the boom extended sideward over a canal.

Again, a point sufficiently close to the far side of a canal being treated generally is a point that is no more than one-tenth of the canal width away from the far side of a canal as measured along the horizontal. This is illustrated in FIG. 6 in which there is shown diagrammatically a trailer 452 having a boom 476 (having a distal end 412) extending from its first side wall 458 out over a canal 448. The canal 448 holds water 447 between its near side 444 and its far side 446. The canal 448 as shown is twenty feet wide. The phantom line 448*a* denotes the position along the horizontal of the far side 446. The phantom lines 448*b* and 448*c* denote points along the horizontal that are one-tenth of the width of the canal 448 away from the far side 446. In other words, phantom lines 448*b* and 448*c* are each spaced apart from phantom line 448*a* by a distance of two feet. The phantom lines 448*b* and 448*c* delineate the boom-end zone in which the distal end 412 should preferably be situated or positioned, which, as illustrated in FIG. 6, it does. As seen in FIG. 6, whether or not the distal end 412 will be positioned or situated in the boom-end zone between phantom lines 448*b* and 448*c* depends on (a) the width of the canal 448, (b) the overall length of the boom 476 and (c) the distance between the first side wall 458 of the trailer 452 and the near side 444 of the canal 448. The latter of course depends on how close or far the trailer 452 is running from the canal 448. Generally in the present method, a trailer with its boom extended sideward will be traveling alongside a canal, and the gap between the trailer and the canal will be from about one to about fifteen feet (most typically from three to fifteen feet). Further, as seen in FIG. 6, the boom-end zone defined by phantom lines 448*b* and 448*c* extends past the far side 446 (delineated with phantom line 448*a*) and the situation in which the boom's distal end 412 extends beyond the far side 446 of the canal 448 is not excluded from even preferred embodiments of the present invention provided that, for practical and safety reasons, the discharge of calcium hypochlorite from the system it supports is to the surface of the water 447 and not to the ground 440 adjacent the far side 446 of the canal 448.

Figure 7:
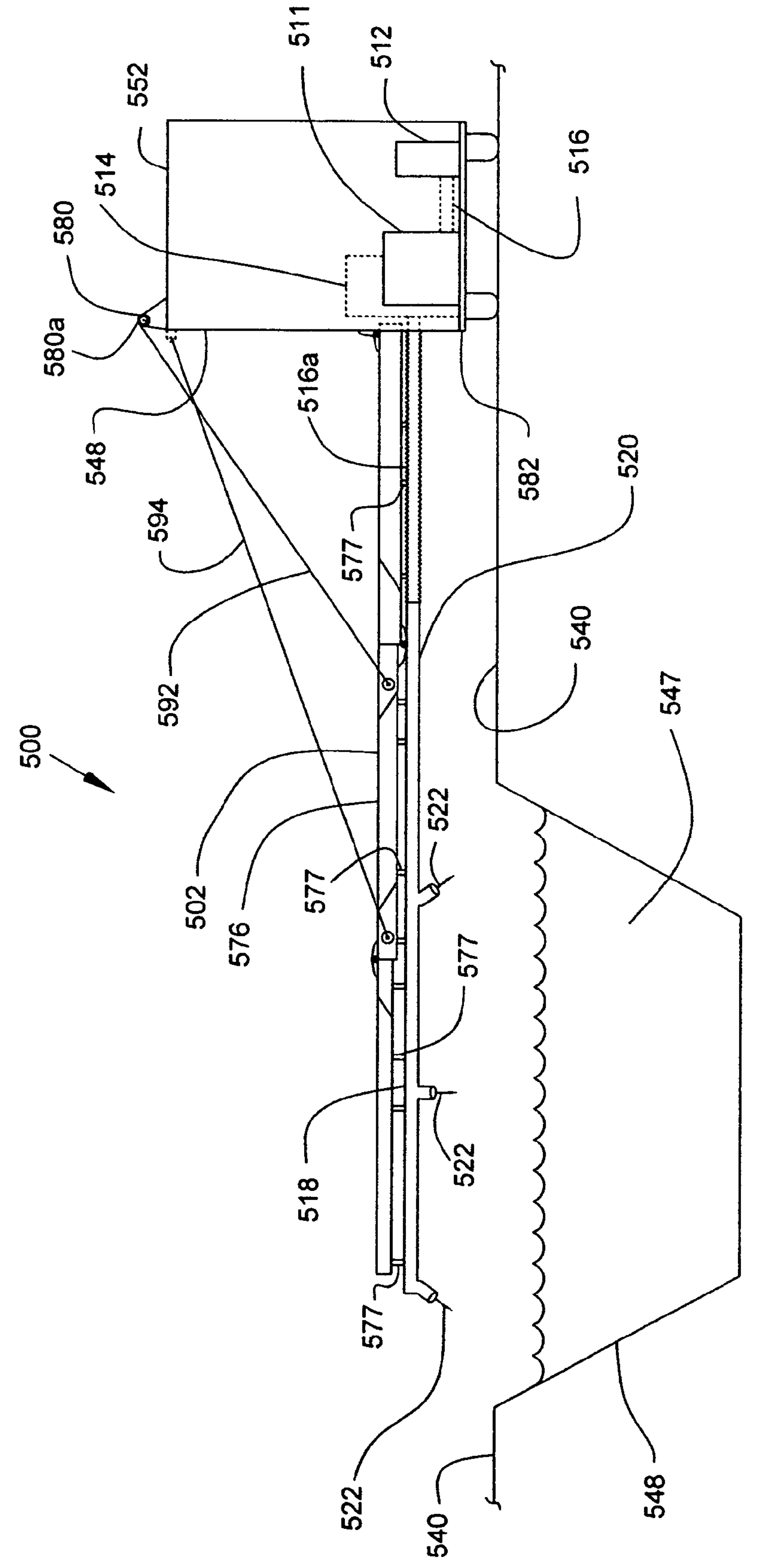
FIG. 7 is a partially diagrammatic view of the mobile unit of the present invention shown with the boom extended sideward over a canal.

Referring now to FIG. 7, there is shown a mobilized device and delivery system 500 of the present invention, shown alongside a canal 548 with its boom 576 extended sideward from the first side 548 of a mobile unit 552. (Here the mobile unit 552 could be a motorized trailer or truck-style vehicle, or instead a towed trailer shown without the tow truck.) The boom 576 is held extended sideward by cable 592 which runs from the boom's middle segment 502 up to the grooved wheel 580*a* of the pulley 580 on the mobile unit 552. A tubular arm 516 is shown suspended from the boom 576 by a plurality of cords, straps or ties 577 (that is, conventional strap-like mechanical fasteners which conveniently may be bungee cords or the like). The tubular arm 516 as shown extends sideward a slight distance farther than the boom 576. (Generally, a boom can have a sideward reach that is about ten percent less or ten percent more than the sideward reach of a tubular arm, although there is no practical reason for a boom to have a sideward reach longer than a tubular arm except the savings in time and effort if a given boom can be used with a given tubular arm without changing its length by changing the segments.) Seated on the platform 582 of the mobile unit 552 are the generator 511 which powers the pulley 580 and the blower 512. Inside of the mobile unit 552 is the hopper 514 (shown in phantom). Also inside of the mobile unit 552, and (shown in phantom) is the proximal end 520 of the tubular arm 516. The tubular arm 516 at its proximal end 520 runs into the mobile unit 552, past the hopper 514 (which feeds calcium hypochlorite to it via structures such as those described above but not illustrated in this FIG. 6), to the blower 512. A six to ten foot section of the tubular arm, which section is designated with the reference numeral 516*a*, is constructed from a flexible, non-corrosive material to allow the tubular arm section 516*a* to flex as the boom 576 is raised and/or lowered. The boom 576 and the tubular arm 516 together extend sideward from the mobile unit 552 across the ground 540 to, and almost across, a canal 548. Ports or conduits 522 are shown directing calcium hypochlorite-entrained air streams 518 to the surface of the water 547 in the canal 548. Other features shown are equivalent to like features described in detail above, and are not, and need not, be described further as to this FIG. 7.

The device of the present invention in preferred embodiments, particularly the mobile unit with its appurtenances and adjuncts described above, when deployed according to the present method, provides a uniform distribution, delivery or scattering of calcium hypochlorite solid to and along a canal. In preferred embodiments, this uniform distribution or scattering is a fine dispersal of calcium hypochlorite solid to and along a canal, as discussed above. The attainment or realization of such a uniform delivery of a fine dispersal of calcium hypochlorite solid to a canal is the core factor providing outstanding remediation of problematic levels of organic debris such as algae and other biological materials.

In preferred embodiments of the invention, not only is a uniform delivery of a fine dispersal of calcium hypochlorite solid to a canal realized, it is realized at a very rapid velocity. As the calcium hypochlorite-laden air stream exits the delivery system and approaches the surface of the water of a canal, it is traveling at a very rapid velocity, as discussed above. The high momentum (mass×velocity) of the calcium hypochlorite particles drives the particles deep into any mats of algae or other organic debris that may be floating on the water's surface, embedding the calcium hypochlorite in the mats. Since the embedded calcium hypochlorite particles are solid, they slowly dissolve within these mats. This slow dissolution provides a concentrated, controlled release of chlorine. This slow dissolution initiates and enables a chlorine liberation system that oxidizes and thus kills the algae or other organic debris from within a floating mat or other floating mass.

The high momentum of the calcium hypochlorite particles as they are propelled as provided in preferred embodiment by the device and method of the present invention also enables a practical and efficient treatment of the sides and the bottom of a canal where algae and other organic debris adhere and grow. In preferred embodiments of the invention, the calcium hypochlorite-laden air stream is propelled and directed to the sides and the bottom of a canal, and the calcium hypochlorite particles are driven into the biological growth adhering to the sides of a canal, even into such biological growth adhering to a canal side below the water surface. Treatment of organic debris adhering below the water surface to the sides of a canal sides is of particular significance and value because it is difficult to accomplish with conventional treatments and techniques, which is discussed in more detail below. Again, in the same or analogous manner discussed above regarding floating mats, the calcium hypochlorite particles, which have been driven into the organic debris adhering to the sides and/or bottom of a canal, are embedded in the debris and there they slowly dissolve, providing a concentrated, controlled release of chlorine, and initiating and enabling a chlorine liberation system that oxidizes and thus kills the algae or other organic debris from within.

In other words, in preferred embodiments of the process of the present invention, the air/calcium hypochlorite dispersion matrix (air stream with entrained calcium hypochlorite) hits the floating organic debris, such as an algae mat, and the calcium hypochlorite particles are driven into, and impregnate, the algae/water matrix of such algae mat. The air dissipates, leaving the calcium hypochlorite particles imbedded in the water/algae matrix. The calcium hypochlorite particles begin to wet and liberate chlorine that dissolves into the water. Since these small calcium hypochlorite particles are impregnated into and around the algae, a controlled chlorine-release mechanism is established. This results in a localized and very concentrated chlorine solution proximate to the algae or other organic debris that is extremely more effective in killing the algae and otherwise decomposing organic debris than the same amount of chlorine dispersed or distributed more widely through the canal water. For example, a solution of bleach of ultimately the same chlorine concentration delivered in an analogous method would be far less effective in decomposing algae mats because the bleach solution would rapidly dissipate in the water surrounding the algae. In preferred embodiments of the present method, the calcium hypochlorite remains in direct contact with the algae for extended periods of time as the particles slowly wet, dissolve and begin to react. Particles are sometimes still interacting and reacting with the algae and algae mats hours after they have been imbedded, entrained or impregnated into the water/algae matrix. Although calcium hypochlorite reacts quickly with water, it is the wetting/dissolution of the calcium hypochlorite particles that is a slow process. This phenomenon of localized controlled release of chlorine makes the method of the present invention unique and extremely effective in the decomposition of floating organic debris such as algae mats.

When the algae or other organic debris is below the surface of the water, for instance on the sides or bottom of a canal, the air/calcium hypochlorite dispersion matrix (air stream with entrained calcium hypochlorite) hits the water surface and the calcium hypochlorite particles rapidly settle out onto and into the algae or other organic debris beneath the surface of the water. The speed of the solid particles hitting the water surface dramatically enhances this settling process. Again here, the calcium hypochlorite particles are slowly wetted and the same controlled release phenomenon takes place resulting in a relatively localized and very effective killing or other decomposition of algae or other organic debris beneath the water's surface.

In comparison, the even, consistent and comprehensive remediation of organic debris in a canal provided by the device and method of the present invention has not been, and cannot be, achieved by conventional canal-treatment regimes. As discussed above, there are three conventional types of treatment additives, namely: (a) chlorine gas; (b) acrolein (such as the commercial Magnacide® product); and (c) copper sulfate and/or chelated copper products. The conventional canal-treatment regimes for each of these three types of additives are point additions at spatial intervals along the length of a canal. Such point additions of chlorine gas or acrolein are normally sub-water-surface additions because a release of the volatiles of these noxious chemicals to atmosphere would be harmful, and possibly lethal, to life forms in the area and intolerably environmentally toxic. In any instance, such point additions introduce the treatment chemical intended for an extensive canal section entirely at a single point and then depend on the movement of the water, and of course to a lesser extent on the normal dispersion of a water-soluble chemical in the water, for the delivery of the chemical downstream of its introduction point. Such point additions are typically made at locations that are about two to five miles apart along the length of a canal, and usually involve the underwater release of the treatment chemical continuously for several hours. Such point additions are repeated at intervals depending on how fast algae and/or other organic debris re-infest the canal. For acrolein-based treatments, for instance, the time interval between point treatments usually is from about seven to about ten days.

Such point addition, namely the prolonged and usually underwater release of a chemical at a single point for the treatment of typically hundreds of thousands of square feet of canal, causes inconsistent treatment-chemical availabilities and uneven remediation for multiple reasons. For instance, the typical canal profile is a blunted V-shape, such as is seen in FIG. 6. In a canal with such a profile, the water flow is predominantly down the canal's center, and therefore the concentration of treatment chemical which reaches the canal sides will be less than that in interior canal sections. Even in a canal with substantially upright sides, the water will flow faster down the center than along the sides or the bottom. Further, regardless of a canal's profile, the chemical concentration will decline with the distance from the point of introduction (point of release or injection), both because of the chemical's dilution as it spreads out and because of the chemical's consumption depletion. Moreover, these concentration gradients will persist despite any boosting of the amount of chemical released at the addition point.

These concentration gradients are particularly problematic for the treatment of the normally predominant organic debris, namely algae and aquatic weeds, and this factor is best understood in the context of canal dynamics. Canal conditions are continually in transition. At the onset of the irrigation (growing) season the water of a canal is usually clean, because the canal had been emptied and cleaned out at the end of the prior irrigation season. The water of a canal might also be relatively clean after a chemical treatment during the growing season (depending on the treatment). But because canals are open waterways, their waters rapidly become fouled as discussed above. Weeds root in the soil that is blown into the canal during the growing season, but since weeds are rooted they stay in place (they are stationary or site-fixed) and do not themselves cause any significant canal fouling problems unless the growth is substantial enough to choke off the water flow of the canal, which can be an issue with certain types of weeds (referred to as target weeds) such as American pond weed and Sago pond weed. Further, the site-immobility of aquatic weeds, regardless of type, in combination with the expanse of underwater surfaces such weeds present, generally sparks algae-driven problems because algae will adhere to, and build up on, those surfaces. It is important to treat the target weeds while they are young or in their "non-woody" stage so that these types of weeds are controlled and their growth is inhibited. Such early-growth stage treatment will reduce the ability of target weeds to proliferate and choke off the water flow of the canal. Such early-growth stage treatment is also efficacious in the control of other, non-target, aquatic weeds. Algae, on the other hand, has no root system and therefore it can develop anywhere. Algae is site-fixed only to the extent and degree to which it adheres to site-immobile surfaces. Algae therefore can succeed and flourish throughout a canal.

Further, algae proliferates in slow-flowing water, or in other words, slow-flowing water is conducive to algae growth. Since canal water flows faster down the center of the canal and slower down the sides and bottom of the canal, algae almost inevitably will develop along the canal's sides and bottom, including algae proliferations on the surfaces of weeds when weeds are present. As the mass of these algae deposits increases, patches get larger and begin appearing on the water surface. As these algae deposits become even larger, they begin to break off as small patches that start floating down the canal. This is where the primary problem occurs and why canal treatment is required for algae. As water is drawn from the canal into the grower's pumping system, the algae are floating free with the water fouls the filter screens at the growers' irrigation-water intake system, upstream of the growers' irrigation pump. When a filter screen is fouled, too little water (and in some cases no water) is being pumped from the canal by the irrigation pump, which can damage the irrigation pump itself in addition to the crop damage caused by a lack of sufficient irrigation water. The fouled irrigation screen must be manually cleaned, and that cleaning requires a shut down of the irrigation system. An irrigation-system shut down is very costly both in terms of the labor required and the loss of irrigation time since many growers are irrigating either twenty-four hours a day or during time periods when energy costs are the least expensive, such as at night or at other non-peak hours. Another problem arises when the canal water contains algae at levels that, although not high enough to plug the irrigation screens, are sufficiently high to plug the sand media filters that are placed after (downstream of) the irrigation pumps. The sand media filters are in place to filter out, and thus protect the irrigation system from, any and all types of particles, including but not limited to algae. When the sand media filters begin to plug, they normally back flush automatically. While this automatic back-flush technology clears the sand media filter (which in turn is preventing particles from entering a growers' irrigation system), its activation is detrimental to canal-water quality because the back-flush, with its huge load of inoculum, is normally discharged into the canal downstream of the grower's water intake system. A back-flush discharge will severely increase the rate of algae formation and growth further down the canal.

Another algae-based problem occurs in the vicinity of road crossings, where a canal is routed under a road in the field or under public roads. The canal-routing under a road is usually through an underground culvert or pipe. If the water flow through such a culvert or underground pipe is restricted due to accumulating algae deposits (which are not uncommon, particularly on the intake side of the culvert or pipe), the water overflows the canal banks causing significant problems and damage to both the canal and adjacent fields as discussed earlier.

Canal dynamics therefore routinely thwart conventional point addition of chemical treatments, particularly regarding algae problems. Algae proliferates in areas of slower flowing water, such as the canal sides and bottom, while point additions heavily rely on water flow to disperse the chemical. The treatment concentrations reaching the canal sides and bottom are invariably deficient for the algae loading found there, particularly regarding the sides and bottom regions that are significantly remote from any point-addition site. Further, detached mats of algae float along with the water, and the mats which do not pass a point addition site during the chemical release are at best being "chased" by the chemical-treatment dispersion. And further still, areas requiring heavier dosages of treatment chemical, such as canal-routings under road crossings, are receiving only a declining level of treatment chemical some point along its declining concentration gradient. These point additions therefore do not completely kill the floating algae mats or the algae proliferations along the sides and bottom which give rise to the floating algae, and do not completely clean out the canal-routings under road crossings. These shortcomings of point additions are multiplied under all-too-common slow water flow conditions. Under slow water flow conditions, algae proliferation is heightened and treatment-chemical distribution is diminished.

In contrast to the conventional point-addition approach necessarily taken in the treatment of canals with any of the conventional canal-treatment chemicals, the present invention: (a) can, and preferably does, treat the entire surface of a canal; (b) can be, and preferably is, variable so that higher dosages are delivered to areas of higher organic-debris infestations; (c) is not deleteriously impacted by low water flow conditions; and (d) in preferred embodiments, impregnates organic-debris masses, such as algae mats and aquatic weeds, and therein slowly releases chlorine from within for more effective decomposition of the surrounding mass.

Moreover, the present invention, after chlorine release and consumption in the process of decomposing organic debris, introduces only low levels of chloride and calcium to the canal water. The chloride levels which are introduced by the treatment are much lower than the chloride levels typically in the canal water already. The calcium levels which are introduced are not only also very small but also beneficial because calcium is beneficial to agricultural soil, which is the ultimate destination of agricultural canal water.

In contrast to the inconsistent distribution concentrations (concentration gradients) and uneven remediation levels provided by point addition of treatment chemicals discussed above, and the frequent regrowth and proliferation of algae seen within a few days, the present invention efficiently delivers solid calcium hypochlorite particles and uniformly decomposes organic debris throughout the canal cost-effectively and safely. The present invention sufficiently decontaminates the canal water to provide canal-delivered water of sufficient cleanliness that it requires no, or only nominal, further clean-up by individual growers, which unburdens the growers and/or increases agricultural productivities.

EXAMPLE 1

The device and method of the present invention were employed to treat a canal, and visual observations of the amount of algae present in the canal before this treatment, and periodically after this treatment, are set forth in Tables 1-3 below. (The visual observations are accurate and realistic evaluations because the visual amount of algae in the canal correlates well to actual biological-debris problems.) This canal is fed from a large water reservoir which has about thirty percent of its surface covered with algae. This canal is therefore continuously being inoculated with algae which enters with the source water. The flow rate of the water when entering the canal is about one hundred eighty cubic feet per second. Due to water usage from the various growers along the canal, this initial water flow rate decreases at points along the canal, and then decreases dramatically over the last mile to about twenty cubic feet per second. This canal is a typical example of one which is in need of treatment to remediate organic debris. Prior to the treatments of this Example 1, this canal was being point treated with acrolein every eight to ten days during the height of the irrigation season to obtain a satisfactory treatment. In this Example 1, the canal was treated three times along substantially its entire length by propelling a calcium hypochlorite-entrained air stream to the water surface and to the sides of the canal from a delivery system suspended off a mobile unit as described above. An operator made visual assessments of the degree of organic debris build-up along the canal and adjusted the concentration of calcium hypochlorite in the air stream accordingly. The pre-treatment and post-treatment conditions of the canal are shown in Tables 1, 2 and 3 below where the visual assessment of organic debris, made at each quarter mile along the length of the canal, are reported at: (a) just before treatment; (b) twelve hours after the treatment; (c) about a week (seven or eight days) after the treatment; and about a week and a half (ten, twelve and ten days, respectively) after treatment. The just before treatment assessment for the second and third treatments set forth in Tables 2 and 3 below are also continued-assessments of the prior treatment (i.e., the T2-b observations in Table 2 are the same as the T1-10d observations in Table 1, and the T3-b observations in Table 3 are the same as the T2-12d observations in Table 2). Further, any relative terms in an observation refer to the prior observation made at the given time; for example, the "slightly larger patches" observation under T1-10d at 0.75 to 1.00 miles in Table 1 below refers to the patches being slightly larger than the patches observed at T1-10d at 0.50 to 0.75 miles, and not to the canal condition observed at T1-7d at 0.75 to 1.00 miles.

TABLE 1

| Miles/T # | Canal Description (at point (miles) along canal at T #) |
|---|---|
| | Treatment 1 Impact<br>Just before Treatment 1 (T1-b), after 12 hr. (T1-12 h), after 7 days (T1-7 d), after 10 days (T1-10 d) |
| | 0.00 to 0.25 miles |
| T1-b | Small amount of algae is growing on the water surface of the canal and along the sides and bottom of the canal. |
| T1-12 h | Canal visually free of algae. |
| T1-7 d | Clear, visually free of algae. |
| T1-10 d | Slight amount of algae is growing along the sides of the canal. |
| | 0.25 to 0.50 miles |
| T1-b | Slightly larger patches beginning to develop on the water surface of the canal and significant levels on the sides and bottom of the canal |
| T1-12 h | Canal visually free of algae. |
| T1-7 d | Clear, visually free of algae. |
| T1-10 d | Slight amount of algae is growing on the water surface and along the sides of the canal. |
| | 0.50 to 0.75 miles |
| T1-b | Larger patches of algae on the water surface and algae growing up from the sides and bottom of the canal. |
| T1-12 h | Canal visually free of algae. |
| T1-7 d | Clear, visually free of algae. |
| T1-10 d | Small amount of algae is growing on the water surface and along the sides of the canal. |
| | 0.75 to 1.00 miles |
| T1-b | Large patches of algae on the water surface and slightly more algae is growing up from the sides and bottom of the canal. |
| T1-12 h | Canal visually free of algae. |
| T1-7 d | Clear, visually free of algae. |
| T1-10 d | Slightly larger patches of algae are growing on the water surface and along the sides of the canal. |
| | 1.00 to 1.25 miles |
| T1-b | Still patches of algae are floating on the surface, but now the algae growing on the sides extents almost up to the water surface. |
| T1-12 h | Canal visually free of algae. |
| T1-7 d | Clear, visually free of algae. |
| T1-10 d | Slightly larger patches of algae is growing on the water surface and along the sides of the canal. |
| | 1.25 to 1.50 miles |
| T1-b | Algae patches floating on the water surface cover approximately 5 percent of the water surface and algae growing on the sides extends up to water surface. |
| T1-12 h | Canal visually free of algae. |
| T1-7 d | Clear, visually free of algae. |
| T1-10 d | Slightly larger patches of algae are growing on the water surface and along the sides of the canal. |
| | 1.50 to 1.75 miles |
| T1-b | Algae patches floating on the water surface still cover approximately 5 percent of the water surface. Algae growing on the sides of the canals extend to the surface and there is more algae that is completely covering the bottom of the canal. Also, there is significant algae is covering the screens along the canal where the growers' irrigation pumps withdraw water from the canal. |
| T1-12 h | Canal visually free of algae. |
| T1-7 d | Slight amount of algae is growing on the water surface of the canal. |
| T1-10 d | Algae patches floating on the water cover about 1 percent of the water surface. More algae is growing on the sides of the canal. |
| | 1.75 to 2.00 miles |
| T1-b | Algae patches floating on the water surface cover slightly more than 5 percent of the canal. More algae is growing up from the canal sides and more algae is growing on the bottom of the canal. There is still significant algae covering the screens along the canal where the growers' irrigation pumps withdraw water from along the canal. |
| T1-12 h | Canal visually free of algae. |
| T1-7 d | Clear, visually free of algae. |
| T1-10 d | Algae patches floating on the water cover about 1 percent of the canal surface. Even more algae is growing on the sides of the canal. Small amount of algae is covering the screens along the canal where the growers' irrigation pumps withdraw water from the canal. |

TABLE 1-continued

| Miles/T # | Canal Description (at point (miles) along canal at T #) |
| --- | --- |
| | Treatment 1 Impact<br>Just before Treatment 1 (T1-b), after 12 hr. (T1-12 h), after 7 days (T1-7 d), after 10 days (T1-10 d) |
| | 2.00 to 2.25 miles |
| T1-b | Algae patches floating on the water surface cover slightly less than about 10 percent of the canal. Algae growing up from the sides are beginning to combine with the floating algae patches. Significant algae still growing up from the bottom of the canal. Algae is covering the screens leading to the growers' irrigation pumps. |
| T1-12 h | Canal visually free of algae. |
| T1-7 d | Clear, visually free of algae. |
| T1-10 d | Algae floating on the water surface cover approximately 5 percent of the canal. About the same amount of algae growing on the sides of the canal and a slight amount of algae is growing on the bottom of the canal. |
| | 2.25 to 2.50 miles |
| T1-b | Algae patches floating on the water surface cover slightly less than about 10 percent. Algae growing up from the sides are beginning to combine with the floating algae patches. Significant algae still growing up from the bottom of the canal. Algae is covering the screens leading to the growers' irrigation pumps. |
| T1-12 h | Canal visually free of algae. |
| T1-7 d | Slight amount of algae is growing on the water surface of the canal. |
| T1-10 d | Algae floating on the water surface covers slightly more than 5 percent of the canal. About the same amount of algae is growing on the sides of the canal and a slight amount of algae is growing on the bottom of the canal. |
| | 2.50 to 2.75 miles |
| T1-b | Algae patches floating on the water surface covers slightly less than about 10 percent of the canal. Algae growing up from the sides is combining with the floating algae patches to a greater extent. Significant algae still growing up from the bottom of the canal. Algae is covering the screens leading to the growers, irrigation pumps. |
| T1-12 h | Canal visually free of algae. |
| T1-7 d | Slight amount of algae is growing on the water surface of the canal. |
| T1-10 d | Algae floating on the water surface covers more than 5 percent of the canal. About the same amount of algae is growing on the sides of the canal and a slight amount of algae is growing on the bottom of the canal. |
| | 2.75 to 3.00 miles |
| T1-b | Algae on the water surface covers about 15 percent of the canal. Significant amounts of the floating algae are combining with the algae from the sides, and algae growing in the bottom of the canal is almost growing up to the water surface. Still significant algae is covering growers' irrigation pump intake screens. |
| T1-12 h | Canal visually free of algae. |
| T1-7 d | Slight amount of algae is growing on the water surface of the canal. |
| T1-10 d | Algae on water surface covers approximately 10 percent of the canal. Small amount of algae is growing on the sides and bottom of the canal. Small amount of algae is covering growers' irrigation pump intake screens. |
| | 3.00 to 3.25 miles |
| T1-b | Algae on the water surface covers about 15 percent of the canal. Significant amounts of the floating algae are combining with the algae from the sides, and algae growing in the bottom of the canal is almost growing up to the water surface. Still significant algae is covering growers' irrigation pump intake screens. |
| T1-12 h | Canal visually free of algae. |
| T1-7 d | Slight amount of algae is growing on the water surface of the canal. |
| T1-10 d | Algae on water surface covers approximately 10 percent of the canal. Small amount of algae is growing on the sides and bottom of the canal. Small amount of algae is covering growers' irrigation pump intake screens. |
| | 3.25 to 3.50 miles |
| T1-b | Algae on the water surface covers about 20 percent of the canal. Significant amounts of the floating algae are combining with the algae from the sides, and algae growing in the bottom of the canal is almost growing up to the water surface. Still significant algae is covering growers' irrigation pump intake screens. |
| T1-12 h | Canal is visually free of algae. |
| T1-7 d | Slight amount of algae is growing on the water surface and along the sides of the canal. |
| T1-10 d | Algae on water surface covers approximately 10 percent of the canal. Small amount of algae is growing on the sides and bottom of the canal. Small amount of algae is covering growers' irrigation pump intake screens. |
| | 3.50 to 3.75 miles |
| T1-b | Algae on water surface covers in excess of 20 percent of the canal. Significant amounts of the floating algae are combining with the algae from the sides, and algae growing in the bottom of the canal is almost growing up to the water surface. Still significant algae is covering growers' irrigation pump intake screens. |
| T1-12 h | Canal visually free of algae. |

TABLE 1-continued

| Treatment 1 Impact<br>Just before Treatment 1 (T1-b), after 12 hr. (T1-12 h), after 7 days (T1-7 d),<br>after 10 days (T1-10 d) | |
|---|---|
| Miles/T # | Canal Description (at point (miles) along canal at T #) |
| T1-7 d | Slight amount of algae is growing on the water surface of the canal. |
| T1-10 d | Algae on water surface covers approximately 10 percent. Small amount of algae is growing on the sides and bottom of the canal. Small amount of algae is covering growers' irrigation pump intake screens. |
| | 3.75 to 4.00 miles |
| T1-b | Algae on the water surface covers in excess of 20 percent of the canal. Significant amounts of the floating algae are combining with the algae from the sides, and algae growing in the bottom of the canal is almost growing up to the water surface. Still significant algae is covering growers' irrigation pump intake screens. |
| T1-12 h | Canal visually free of algae. |
| T1-7 d | Slight amount of algae is growing on the water surface of the canal. |
| T1-10 d | Algae on the water surface is between 10 and 15 percent of the canal. Small amount of algae is growing on the sides and bottom of the canal. Small amount of algae is covering growers' irrigation pump intake screens. |
| | 4.00 to 4.25 miles |
| T1-b | Algae on the water surface covers about 25 percent of the canal. Significant amounts of the floating algae are combining with the with the algae from the sides, and algae growing in the bottom of the canal is almost growing up to the water surface. Still significant algae is covering growers' irrigation pump intake screens. |
| T1-12 h | Canal is visually free of algae. |
| T1-7 d | Slight amount of algae is growing on the water surface of the canal. |
| T1-10 d | Algae on the water surface covers between 10 and 15 percent of the canal. Small amount of algae is growing on the sides and bottom of the canal. Small amount of algae is covering growers' irrigation pump intake screens. |
| | 4.25 to 4.50 miles |
| T1-b | Algae from the bottom is beginning to grow up to the canal water surface and even more of the algae is growing along the side of the canal. It is beginning to become difficult to distinguish the floating algae from that that is combined from the algae growing along the side. Total surface coverage is approaching 30 percent of the canal. Growers' irrigation pump screen plugging is significantly more problematic. |
| T1-12 h | Canal is visually free of algae. |
| T1-7 d | Slight amount of algae is growing on the water surface and along the sides of the canal. |
| T1-10 d | Algae on the water surface covers between 10 and 15 percent of the canal. Small amount of algae is growing on the sides and bottom of the canal. Small amount of algae is covering growers' irrigation pump intake screeens. |
| | 4.50 to 4.75 miles |
| T1-b | Algae from the bottom of the canal is growing up to the canal water surface and even more of the algae is growing along the side of the canal. It is difficult to distinguish the floating algae from that that is combined from the algae growing along the side. Total surface coverage is in excess of 30 percent of the canal. Growers' irrigation pump screen plugging is significantly more problematic. |
| T1-12 h | Canal visually free of algae. |
| T1-7 d | Slight amount of algae is growing on the water surface and along the sides of the canal. |
| T1-10 d | Algae on the canal water surface covers approximately 15 percent. Still small amounts of algae are growing on the sides and bottom of the canal. The amount of algae covering the growers' irrigation pump intake screen is still very minimal. |
| | 4.75 to 5.00 miles |
| T1-b | Significant amount of algae from the bottom of the canal is growing to the surface and is combining with the algae growing from the sides of the canal. Any floating algae is indistinguishable from that growing from the bottom and sides of the canal. Significant algae mats are beginning to form. Canal surface coverage is about 35 percent. Coverage of growers' irrigation pump screens is very problematic. |
| T1-12 h | Small amounts of discolored/dying algae are adhering to the bottom of the canal. |
| T1-7 d | Slight amount of algae is growing on the water surface and along the sides of the canal. |
| T1-10 d | Algae covers in excess of 15 percent of the canal water surface and there is more algae growing up from the bottom and sides of the canal. |
| | 5.00 to 5.25 miles |
| T1-b | Significant amount of algae from the bottom of the canal is growing to the surface and is combining with the algae growing from the sides of the canal. Any floating algae is indistinguishable from that growing from the bottom and sides. Significant algae mats are beginning to form. Canal surface coverage is about 40 percent. Coverage of growers' pump screens is very problematic. |
| T1-12 h | Small amounts of discolored/dying algae are adhering to the bottom of the canal. |

TABLE 1-continued

| Treatment 1 Impact<br>Just before Treatment 1 (T1-b), after 12 hr. (T1-12 h), after 7 days (T1-7 d), after 10 days (T1-10 d) | |
|---|---|
| Miles/T # | Canal Description (at point (miles) along canal at T #) |
| T1-7 d | Slight amount of algae is growing on the water surface and along the sides of the canal. |
| T1-10 d | Algae covers slightly less than 20 percent of the canal water surface and there is slightly more algae growing up from the bottom and sides of the canal. |
| | 5.25 to 5.50 miles |
| T1-b | Significant amount of algae from the bottom of the canal is growing to the surface and is combining with the algae growing from the sides of the canal. Any floating algae is indistinguishable from that growing from bottoms and sides of the canal. Significant algae mats are beginning to form. Canal surface coverage is about 45 percent. Coverage of growers' irrigation pump screens is very problematic. |
| T1-12 h | Small amounts of discolored/dying algae are adhering to the bottom of the canal. |
| T1-7 d | Slight amount of is algae is growing on the water surface and along the sides and bottom of the canal. |
| T1-10 d | Algae covers slightly less than 20 percent of the canal water surface and there is slightly more algae growing up from the bottom and sides of the canal. None of the algae on the sides of the canal have reached the water surface. |
| | 5.50 to 5.75 miles |
| T1-b | Significant amount of algae from the bottom of the canal is growing to the surface and is combining with the algae growing from the sides of the canal. Any floating algae is indistinguishable from that growing from the bottom and sides of the canal. Significant algae mats are beginning to form. Canal surface coverage is about 45 percent. Coverage of growers' irrigation pump screens is very problematic. |
| T1-12 h | Small amounts of discolored/dying algae are adhering to bottom of the canal. |
| T1-7 d | Slight amount of algae is growing on the water surface and along the sides and bottom of the canal. |
| T1-10 d | Algae covers slightly less than 25 percent of the canal water surface and there is slightly more algae growing up from the bottom and sides of the canal. None of the algae on the sides of the canal have reached the water surface. |
| | 5.75 to 6.00 miles |
| T1-b | Significant amount of algae from the bottom of the canal is growing to the surface and is combining with the algae growing from the sides of the canal. Any floating algae is indistinguishable from that growing from the bottom and sides. Significant algae mats are beginning to form. Canal surface coverage is about 45 percent of the canal. Coverage of growers' irrigation pump screens is very problematic. |
| T1-12 h | Small amounts of discolored/dying algae are adhering to the bottom and sides of the canal. |
| T1-7 d | Slight amount of algae is growing on the water surface and along the sides and bottom of the canal. |
| T1-10 d | Algae covers slightly less than 25 percent of the canal water surface and there is slightly more algae growing up from the bottom and sides of the canal. The algae growing on the sides of the canal is just beginning to reach the water surface. Algae on the bottom of the canal is slightly greater. There is more algae on the growers' irrigation pump intake screens, but the algae is not problematic. |
| | 6.00 to 6.25 miles |
| T1-b | Significant amount of algae from the bottom of the canal is growing to the surface and is combining with the algae growing from the sides of the canal. Any floating algae is indistinguishable from that growing from the bottom and sides. Significant algae mats are beginning to form. Canal surface coverage is about 50 percent. Coverage of growers' irrigation pump screens is very problematic. |
| T1-12 h | Small amounts of discolored/dying algae are adhering to the bottom and sides of the canal. |
| T1-7 d | Slight amount of algae is growing on the water surface and along the sides and bottom of the canal. |
| T1-10 d | Algae covers slightly less more than 25 percent of the canal water surface and there is slightly more algae growing up from the bottom and sides of the canal. In some areas the algae growing on the sides of the canal is just beginning to reach the water surface of the canal. Algae on the bottom of the canal is slightly greater. There is more algae on the growers' irrigation pump intake screens, but the algae is not problematic. |
| | 6.25 to 6.50 miles |
| T1-b | Significant amount of algae from the bottom of the canal is growing to the surface and is combining with the algae growing from the sides of the canal. Any floating algae is indistinguishable from that growing from the bottom and sides. Significant algae mats are beginning to form. Canal surface coverage is about 50 percent. Coverage of growers' irrigation pump screens is very problematic. |

TABLE 1-continued

Treatment 1 Impact
Just before Treatment 1 (T1-b), after 12 hr. (T1-12 h), after 7 days (T1-7 d), after 10 days (T1-10 d)

| Miles/T # | Canal Description (at point (miles) along canal at T #) |
|---|---|
| T1-12 h | Small amounts of discolored/dying algae are adhering to the bottom and sides of the canal. |
| T1-7 d | Slight amount of algae is growing on the water surface and along the sides and bottom of the canal. |
| T1-10 d | Algae coverage is about 30 percent of the water surface of the canal. Algae on the sides of the canal has reached the surface. The algae down the center of the canal is just reaching the surface. |
| | 6.50 to 6.75 miles |
| T1-b | Significant amount of algae from the bottom of the canal is growing to the surface and is combining with the algae growing from the sides of the canal. Any floating algae is indistinguishable from that growing from the bottom and sides of the canal. Significant algae mats are beginning to form. Canal surface coverage is about 55 percent. Coverage of growers' irrigation pump screens is very problematic. |
| T1-12 h | Small amounts of discolored/dying algae are adhering to the bottom and sides of the canal. Small patches of dead algae are floating on the canal and are covering about 1 to 2 percent of the water surface. |
| T1-7 d | Small amount of algae is growing on the water surface. Slight amount of algae is growing along the sides and bottom of the canal. |
| T1-10 d | Algae coverage is about 30 percent of the water surface of the canal. Algae on the sides of the canal has reached the surface. The algae down the center of the canal is just reaching the surface. |
| | 6.75 to 7.00 miles |
| T1-b | Significant amount of algae from the bottom of the canal is growing to the surface and is combining with the algae growing from the sides of the canal. Any floating algae is indistinguishable from that growing from the bottom and sides of the canal. Significant algae mats are beginning to form. Canal surface coverage is about 55 percent. Coverage of growers' irrigation pump screens is very problematic. |
| T1-12 h | Small amounts of discolored/dying algae are adhering to the bottom and sides of the canal. Small patches of dead algae are floating on the canal and are covering about 3 to 5 percent of the water surface. |
| T1-7 d | Small amount of algae is growing on the water surface. Small amount of algae is growing along the sides and bottom of the canal. |
| T1-10 d | Algae coverage is about 30 percent of the water surface of the canal. Algae on the sides of the canal has reached the surface. The algae down the center of the canal is just reaching the surface. |

TABLE 2

Treatment 2 Impact
Just before Treatment 2, which was 10 days after Treatment 1, (T2-b), after 12 hr. (T2-12 h), after 8 days (T2-8 d), after 12 days (T2-12 d)

| Mile/T # | Canal Description (at point (miles) along canal at T #) |
|---|---|
| | 0.00 to 0.25 miles |
| T2-b | Slight amount of algae is growing along the sides of the canal. |
| T2-12 h | Canal visually free of algae. |
| T2-8 d | Clear, visually free of algae. |
| T2-12 d | Very slight amount of algae is growing along the sides of the canal. |
| | 0.25 to 0.50 miles |
| T2-b | Slight amount of algae is growing on the water surface and along the sides of the canal. |
| T2-12 h | Canal visually free of algae. |
| T2-8 d | Clear, visually free of algae. |
| T2-12 d | Slight amount of algae is growing along the sides of the canal. |
| | 0.50 to 0.75 miles |
| T2-b | Small amount of algae is growing on the water surface and along the sides of the canal. |
| T2-12 h | Canal visually free of algae. |
| T2-8 d | Clear, visually free of algae. |
| T2-12 d | Slight amount of algae is growing along the sides of the canal. |
| | 0.75 to 1.00 miles |
| T2-b | Slightly larger patches of algae are growing on the water surface and along the sides of the canal. |
| T2-12 h | Canal visually free of algae. |

TABLE 2-continued

| Treatment 2 Impact<br>Just before Treatment 2, which was 10 days after Treatment 1, (T2-b),<br>after 12 hr. (T2-12 h), after 8 days (T2-8 d), after 12 days (T2-12 d) | |
|---|---|
| Mile/T # | Canal Description (at point (miles) along canal at T #) |
| T2-8 d | Clear, visually free of algae. |
| T2-12 d | Slight amount of algae is growing on the water surface and along the sides and bottom of the canal. |
| | 1.00 to 1.25 miles |
| T2-b | Slightly larger patches of algae are growing on the water surface and along the sides of the canal. |
| T2-12 h | Canal visually free of algae. |
| T2-8 d | Clear, visually free of algae. |
| T2-12 d | Slight amount of algae is growing on water surface and along the sides and bottom of the canal. |
| | 1.25 to 1.50 miles |
| T2-b | Slightly larger patches of algae are growing on the water surface and along the sides and bottom of the canal. |
| T2-12 h | Canal visually free of algae. |
| T2-8 d | Clear, visually free of algae. |
| T2-12 d | Slight amount of algae is growing on water surface and along the sides and bottom of the canal. |
| | 1.50 to 1.75 miles |
| T2-b | Algae patches floating on the water cover about 1 percent of the water surface. More algae is growing on the sides of the canal. |
| T2-12 h | Canal visually free of algae. |
| T2-8 d | Clear, visually free of algae. |
| T2-12 d | Slightly more algae is growing on water surface and along the sides of the canal. |
| | 1.75 to 2.00 miles |
| T2-b | Algae patches floating on the water cover about 1 percent of the water surface. Even more algae is growing on the sides of the canal. Small amount of algae is covering the screens along the canal where the growers' irrigation pumps withdraw water from the canal. |
| T2-12 h | Canal visually free of algae. |
| T2-8 d | Clear, visually free of algae. |
| T2-12 d | Slightly more algae is growing on the water surface and along the sides of the canal. Slight amount of algae is growing on the bottom of the canal. Small amount of algae is covering the screens along the canal where the growers' irrigation pumps withdraw water from the canal. |
| | 2.00 to 2.25 miles |
| T2-b | Algae floating on the water surface covers approximately 5 percent of the canal. About the same amount of algae is growing on the sides of the canal and a slight amount of algae is growing on the bottom of the canal. |
| T2-12 h | Canal visually free of algae. |
| T2-8 d | Clear, visually free of algae. |
| T2-12 d | Algae patches present on the water cover about 1 percent of the canal surface. More algae is growing on sides and bottom of the canal. |
| | 2.25 to 2.50 miles |
| T2-b | Algae floating on the water surface covers slightly more than 5 percent of the canal. About the same amount of algae is growing on the sides of the canal and a slight amount of algae is growing on the bottom of the canal. |
| T2-12 h | Canal visually free of algae. |
| T2-8 d | Clear, visually free of algae. |
| T2-12 d | Algae patches present on the water covers more than about 1 percent of canal surface. More algae is growing on sides and bottom of the canal. |
| | 2.50 to 2.75 miles |
| T2-b | Algae floating on the water surface covers more than 5 percent of the canal. About the same amount of algae is growing on the sides of the canal and a slight amount of algae is growing on the bottom of the canal. |
| T2-12 h | Canal visually free of algae. |
| T2-8 d | Clear, visually free of algae. |
| T2-12 d | Algae present on the water surface covers slightly less than about 5 percent of the canal surface. Slightly more algae growing on the sides and bottom of the canal. |
| | 2.75 to 3.00 miles |
| T2-b | Algae on water surface covers approximately 10 percent of the canal. Small amount of algae is growing on the sides and bottom of the canal. Small amount of algae is covering growers' irrigation pump intake screens. |
| T2-12 h | Canal visually free of algae. |
| T2-8 d | Slight amount of algae is growing on the water surface of the canal. |

TABLE 2-continued

| Treatment 2 Impact<br>Just before Treatment 2, which was 10 days after Treatment 1, (T2-b), after 12 hr. (T2-12 h), after 8 days (T2-8 d), after 12 days (T2-12 d) | |
|---|---|
| Mile/T # | Canal Description (at point (miles) along canal at T #) |
| T2-12 d | More algae is growing on the water surface of the canal. Small amount of algae is growing up from the sides and bottom of the canal. Small amount of algae is covering growers' irrigation pump intake screens. |
| | 3.00 to 3.25 miles |
| T2-b | Algae on water surface covers approximately 10 percent of the canal. Small amount of algae is growing on the sides and bottom of the canal. Small amount of algae is covering growers' irrigation pump intake screens. |
| T2-12 h | Canal visually free of algae. |
| T2-8 d | Slight amount of algae is growing on the water surface of the canal. |
| T2-12 d | More algae is growing on the water surface of the canal. Small amount of algae is growing up from the sides and bottom of the canals. Small amount of algae is covering growers' irrigation pump intake screens. |
| | 3.25 to 3.50 miles |
| T2-b | Algae on water surface covers approximately 10 percent. Small amount of algae is growing on the sides and bottom of the canal. Small amount of algae is covering growers' irrigation pump intake screens. |
| T2-12 h | Canal visually free of algae. |
| T2-8 d | Slight amount of algae is growing on the water surface of the canal. |
| T2-12 d | Algae on canal water surface covers about 10 percent of the canal. Slightly more algae is growing on the sides and bottom of the canal. Small amount of algae is covering growers' irrigation pump intake screens. |
| | 3.50 to 3.75 miles |
| T2-b | Algae on water surface covers approximately 10 percent of the canal. Small amount of algae is growing on the sides and bottom of the canal. Small amount of algae is covering growers' irrigation pump intake screens. |
| T2-12 h | Canal visually free of algae. |
| T2-8 d | Slight amount of algae is growing on the water surface of the canal. |
| T2-12 d | Algae on canal water surface covers about 10 percent of the canal. Slightly more algae is growing on the sides and bottom of the canal. Small amount of algae is covering growers' irrigation pump intake screens. |
| | 3.75 to 4.00 miles |
| T2-b | Algae on water surface covers between 10 and 15 percent of the canal. Small amount of algae is growing on the sides and bottom of the canal. Small amount of algae is covering growers' irrigation pump intake screens. |
| T2-12 h | Canal visually free of algae. |
| T2-8 d | Slight amount of algae is growing on the water surface of the canal. |
| T2-12 d | Algae on canal water surface covers more than about 10 percent of the canal. Slightly more algae is growing on the sides and bottom of the canal. Small amount of algae is covering growers' irrigation pump intake screens. |
| | 4.00 to 4.25 miles |
| T2-b | Algae on the water surface covers between 10 and 15 percent of the canal. Small amount of algae is growing on the sides and bottom of the canal. Small amount of algae is covering growers' irrigation pump intake screens. |
| T2-12 h | Canal visually free of algae. |
| T2-8 d | Slight amount of algae is growing on the water surface and along the sides of the canal. |
| T2-12 d | Algae on the canal water surface covers more than 10 percent of the canal. Small amount of algae is growing on the sides and bottom of the canal. Small amount of algae is covering growers' irrigation pump intake screens. |
| | 4.25 to 4.50 miles |
| T2-b | Algae on the canal water surface covers between 10 and 15 percent of the canal. Small amount of algae is growing on the sides and bottom of the canal. Small amount of algae is covering growers' irrigation pump intake screens. |
| T2-12 h | Canal visually free of algae. |
| T2-8 d | Slight amount of algae is growing on the water surface and along the sides of the canal. |
| T2-12 d | Algae on canal water surface is almost 15 percent. Algae on sides of canal almost up to the surface. |
| | 4.50 to 4.75 miles |
| T2-b | Algae on the canal water surfaces covers approximately 15 percent. Still small amounts of algae growing on the sides and bottom of the canal. The amount of algae covering the growers pump intake screen is still very minimal. |
| T2-12 h | Canal visually free of algae. |
| T2-8 d | Slight amount of algae is growing on the water surface and along the sides of the canal. |
| T2-12 d | Algae on canal water surface covers almost 15 percent. Algae on sides of canal is almost up to the surface. |

TABLE 2-continued

| Mile/T # | Canal Description (at point (miles) along canal at T #) |
|---|---|
| | Treatment 2 Impact<br>Just before Treatment 2, which was 10 days after Treatment 1, (T2-b), after 12 hr. (T2-12 h), after 8 days (T2-8 d), after 12 days (T2-12 d) |
| | 4.75 to 5.00 miles |
| T2-b | Algae covers in excess of 15 percent of the canal water surface and there is more algae growing up from the bottom and sides of the canal. |
| T2-12 h | Canal visually free of algae. |
| T2-8 d | Slight amount of algae is growing on the water surface and along the sides of the canal. |
| T2-12 d | Algae on the canal water surface covers approximately 15 percent. Algae on sides and bottom of canal is growing almost up to the water surface. Algae on growers' irrigation pump intake screens is increasing, but not problematic. |
| | 5.00 to 5.25 miles |
| T2-b | Algae covers slightly less than 20 percent of the canal water surface and there is slightly more algae growing up from the bottom and sides of the canal. |
| T2-12 h | Canal visually free of algae. |
| T2-8 d | Slight amount of algae is growing on the water surface and along the sides of the canal. |
| T2-12 d | Algae on the canal water surface covers approximately 15 percent of the canal. Algae on sides and bottom of canal is growing almost up to the water surface. Algae on growers' irrigation pump intake screen is increasing, but not problematic. |
| | 5.25 to 5.50 miles |
| T2-b | Algae covers slightly less than 20 percent of the canal water surface and there is slightly more algae growing up from the bottom of the canal. None of the algae on the sides of the canal have reached the water surface. |
| T2-12 h | Small amounts of discolored/dying algae are adhering to bottom and sides of the canal. |
| T2-8 d | Slight amount of algae is growing on the water surface and along the sides of the canal. |
| T2-12 d | Algae on the canal water surface covers more than 15 percent of the canal. Algae on sides and bottom of canal is growing almost up to the water surface. Algae on growers' irrigation pump intake screens is increasing, but not problematic. |
| | 5.50 to 5.75 miles |
| T2-b | Algae covers slightly less than 25 percent of the canal water surface and there is slightly more algae growing up from the bottom and sides of the canal. None of the algae on the sides of the canal have reached the water surface. |
| T2-12 h | Small amounts of discolored/dying algae are adhering to bottom and sides of the canal. |
| T2-8 d | Slight amount of algae is growing on the water surface and along the sides and bottom of the canal. |
| T2-12 d | Algae on the canal water surface covers about 20 percent of the canal. More algae from the sides and bottom of the canal are reaching the water surface. |
| | 5.75 to 6.00 miles |
| T2-b | Algae covers slightly more than 25 percent of the canal water surface and there is slightly more algae growing up from the bottom and sides of the canal. The algae growing on the sides of the canal is just beginning to reach the water surface. Algae on the bottom of the canal is slightly greater. There is more algae on the growers' irrigation pump intake screens, but the algae is not problematic. |
| T2-12 h | Small amounts of discolored/dying algae are adhering to bottom and sides of the canal. |
| T2-8 d | Slight amount of algae is growing on the water surface and along the sides and bottom of the canal. |
| T2-12 d | Algae on the canal water surface covers about 20 percent of the canal. More algae from the sides and bottom of the canal are reaching the water surface. |
| | 6.00 to 6.25 miles |
| T2-b | Algae covers slightly more than 25 percent of the canal water surface and there is slightly more algae growing up from the bottom and sides of the canal. The algae growing on the sides of the canal is just beginning to reach the water surface. Algae on the bottom of the canal is slightly greater. There is more algae on the growers' irrigation pump intake screens, but the algae is not problematic. |
| T2-12 h | Small amounts of discolored/dying algae are adhering to bottom and sides of the canal. |
| T2-8 d | Slight amount of algae is growing on the water surface and along the sides and bottom of the canal. |
| T2-12 d | Algae on the canal water surface covers about 20 percent of the canal. More algae from the sides and bottom of the canal are reaching the water surface. |

TABLE 2-continued

| Mile/T # | Canal Description (at point (miles) along canal at T #) |
|---|---|
| | Treatment 2 Impact<br>Just before Treatment 2, which was 10 days after Treatment 1, (T2-b), after 12 hr. (T2-12 h), after 8 days (T2-8 d), after 12 days (T2-12 d) |
| | 6.25 to 6.50 miles |
| T2-b | Algae coverage is about 30 percent of the water surface of the canal. Algae on the sides of the canal has reached the surface. The algae down the center of the canal is just reaching the surface. |
| T2-12 h | Small amounts of discolored/dying algae are adhering to bottom of the canal. |
| T2-8 d | Slight amount of algae is growing on the water surface and along the sides and bottom of the canal. |
| T2-12 d | Algae on the water surface covers approximately 25 percent of the canal water surface. Algae from the sides of the canal is beginning to combine with the floating algae on the canal surfaces. |
| | 6.50 to 6.75 miles |
| T2-b | Algae coverage is about 30 percent of the water surface of the canal. Algae on the sides of the canal has reached the surface. The algae down the center of the canal is just reaching the surface. |
| T2-12 h | Small amounts of discolored/dying algae are adhering to bottom and sides of the canal. |
| T2-8 d | Small amount of algae is growing on the water surface. The amount of algae on the sides and the bottom of the canal remains small. |
| T2-12 d | Algae on the water surface covers approximately 25 percent of the canal water surface. Algae from the sides of the canal is beginning to combine with the floating algae on the canal surface. |
| | 6.75 to 7.00 miles |
| T2-b | Algae coverage is about 30 percent of the water surface of the canal. Algae on the sides of the canal has reached the surface. The algae down the center of the canal is just reaching the surface. |
| T2-12 h | Small amounts of discolored/dying algae are adhering to the bottom and sides of the canal. Small patches of dead algae are floating on the canal and are covering about 1 to 2 percent of the water surface of the canal. |
| T2-8 d | Small amount of algae on the water surface. The amount of algae on the sides and the bottom of the canal remains slight. |
| T2-12 d | Algae on the water surface covers approximately 25 percent of the canal water surface. Algae from the sides of the canal is beginning to combine with the floating algae on the canal surface. |

TABLE 3

| Mile/T # | Canal Description (at point (miles) along canal at T #) |
|---|---|
| | Treatment 3 Impact<br>Just before Treatment 3, which was 12 days after Treatment 2, (T3-b), after 12 hr. (T3-12 h), after 7 days (T3-7 d), after 10 days (T3-10 d) |
| | 0.00 to 0.25 miles |
| T3-b | Very slight amount of algae is growing along the sides of the canal. |
| T3-12 h | Canal visually free of algae. |
| T3-7 d | Clear, visually free of algae. |
| T3-10 d | Slight amount of algae is growing along the sides of the canal. |
| | 0.25 to 0.50 miles |
| T3-b | Slight amount of algae is growing along the sides of the canal. |
| T3-12 h | Canal visually free of algae. |
| T3-7 d | Clear, visually free of algae. |
| T3-10 d | Slight amount of algae is growing along the sides of the canal. |
| | 0.50 to 0.75 miles |
| T3-b | Slight amount of algae is growing along the sides of the canal. |
| T3-12 h | Canal visually free of algae. |
| T3-8 d | Clear, visually free of algae. |
| T3-10 d | Slight amount of algae is growing on the water surface and along the sides of the canal. |
| | 0.75 to 1.00 miles |
| T3-b | Slight amount of algae is growing on water surface and along the sides and bottom of the canal. |
| T3-12 h | Canal visually free of algae. |
| T3-7 d | Clear, visually free of algae. |

TABLE 3-continued

Treatment 3 Impact
Just before Treatment 3, which was 12 days after Treatment 2, (T3-b), after 12 hr. (T3-12 h), after 7 days (T3-7 d), after 10 days (T3-10 d)

| Mile/T # | Canal Description (at point (miles) along canal at T #) |
|---|---|
| T3-10 d | Slight amount of algae is growing on the water surface and along the sides of the canal. |
| | 1.00 to 1.25 miles |
| T3-b | Slight amount of algae is growing on water surface and along the sides and bottom of the canal. |
| T3-12 h | Canal visually free of algae. |
| T3-7 d | Clear, visually free of algae. |
| T3-10 d | Slight amount of algae is growing on the water surface and along the sides of the canal. |
| | 1.25 to 1.50 miles |
| T3-b | Slight amount of algae is growing on water surface and along the sides and bottom of the canal. |
| T3-12 h | Canal visually free of algae. |
| T3-7 d | Clear, visually free of algae. |
| T3-10 d | Small amount of algae is growing on the water surface and along the sides of the canal. |
| | 1.50 to 1.75 miles |
| T3-b | Slightly more algae is growing on the water surface and along the sides of the canal. |
| T3-12 h | Canal visually free of algae. |
| T3-7 d | Clear, visually free of algae. |
| T3-10 d | Small patches of algae are floating on the water surface and slightly more algae growing on the sides of the canal. |
| | 1.75 to 2.00 miles |
| T3-b | Slightly more algae is growing on the water surface and along the sides of the canal. Slight amount of algae is growing on the bottom of the canal. Small amount of algae is covering the screens along the canal where the growers' irrigation pumps withdraw water from the canal. |
| T3-12 h | Canal visually free of algae. |
| T3-7 d | Clear, visually free of algae. |
| T3-10 d | Small patches of algae are floating on the water surface and slightly more algae is growing on the sides of the canal. Small amount of algae is covering the growers' intake screens for the irrigation pump. |
| | 2.00 to 2.25 miles |
| T3-b | Algae patches present on the water covers about 1 percent of the canal water surface. More algae is growing on sides and bottom of the canal. |
| T3-12 h | Canal visually free of algae. |
| T3-7 d | Clear, visually free of algae. |
| T3-10 d | Algae patches present on the water cover about 2 percent of the canal surface. |
| | 2.25 to 2.50 miles |
| T3-b | Algae patches present on the water cover more than about 1 percent of the canal water surface. More algae is growing on sides and bottom of the canal. |
| T3-12 h | Canal visually free of algae. |
| T3-7 d | Clear, visually free of algae. |
| T3-10 d | Algae patches present on the water cover more than 2 percent of canal surface. |
| | 2.50 to 2.75 miles |
| T3-b | Algae present on the water surface covers slightly less than about 5 percent of the canal surface. Slightly more algae is growing on the sides and bottom of the canal. |
| T3-12 h | Canal visually free of algae. |
| T3-7 d | Slight amount of algae is growing on the water surface and sides of the canal. |
| T3-10 d | Algae present on the water covers about 5 percent of the canal surface. Slightly more algae is growing on the sides and bottom of the canal. |
| | 2.75 to 3.00 miles |
| T3-b | More algae is growing on the water surface of the canal. Small amount of algae is growing up from the sides and bottom of the canal. Small amount of algae is covering growers' irrigation pump intake screens. |
| T3-12 h | Canal visually free of algae. |
| T3-7 d | Slight amount of algae is growing on the water surface of the canal. |
| T3-10 d | Greater than 5 percent algae is growing on the water surface of the canal. Increased amount of algae is growing up from the sides and bottom of the canal. Small amount of algae is covering growers' irrigation pump intake screens. |

TABLE 3-continued

| Mile/T # | Canal Description (at point (miles) along canal at T #) |
|---|---|
| | Treatment 3 Impact<br>Just before Treatment 3, which was 12 days after Treatment 2, (T3-b), after 12 hr. (T3-12 h), after 7 days (T3-7 d), after 10 days (T3-10 d) |
| | 3.00 to 3.25 miles |
| T3-b | More algae is growing on the water surface of the canal. More algae is growing up from the sides and bottom of the canal. Small amount of algae is covering growers' irrigation pump intake screens. |
| T3-12 h | Canal visually free of algae. |
| T3-7 d | Slight amount of algae is growing on the water surface of the canal. |
| T3-10 d | More algae is growing on the water surface of the canal and is growing up from the sides and bottom of the canal. Small amount of algae is covering growers' irrigation pump intake screens. Large amount of almond leaves is floating on the water surface, adding to the biological debris. |
| | 3.25 to 3.50 miles |
| T3-b | Algae on water surface covers about 10 percent of the canal. Slightly more algae is growing on the sides and bottom of the canal. Small amount of algae is covering growers' irrigation pump intake screens. |
| T3-12 h | Canal visually free of algae. |
| T3-7 d | Slight amount of algae is growing on the water surface and along the sides of the canal. |
| T3-10 d | Algae on water surface covers less than 10 percent of the canal. Fewer leaves are floating on the water surface. Slightly more algae is growing on the sides and bottom of the canal. Small amount of algae is covering growers' irrigation pump intake screens. |
| | 3.50 to 3.75 miles |
| T3-b | Algae on water surface covers about 10 percent of the canal. Slightly more algae is growing on the sides and bottom of the canal. Small amount of algae is covering growers' irrigation pump intake screens. |
| T3-12 h | Canal visually free of algae. |
| T3-7 d | Slight amount of algae is growing on the water surface and along the sides of the canal. |
| T3-10 d | Algae on water surface covers more than 10 percent of the canal. Fewer almond leaves are floating on the water surface. Slightly more algae is growing on the sides and bottom of the canal. Small amount of algae is covering growers' irrigation pump intake screens. |
| | 3.75 to 4.00 miles |
| T3-b | Algae on water surface covers more than 10 percent of the canal. Slightly more algae is growing on the sides and bottom of the canal. Small amount of algae is covering growers' irrigation pump intake screens. |
| T3-12 h | Canal visually free of algae. |
| T3-7 d | Slight amount of algae is growing on the water surface and along the sides of the canal. |
| T3-10 d | Algae on water surfaces covers more than 10 percent of the canal. More algae is growing along the sides and bottom of the canal. |
| | 4.00 to 4.25 miles |
| T3-b | Algae on water surface covers between 10 and 15 percent of the canal. Small amount of algae is growing on the sides and bottom of the canal. Small amount of algae is covering growers' irrigation pump intake screens. |
| T3-12 h | Canal visually free of algae. |
| T3-7 d | Slight amount of algae is growing on the water surface and along the sides of the canal. |
| T3-10 d | Algae on water surfaces covers more than 10 percent of the canal. Algae on the sides and bottom of canal is growing almost up to the water surface. |
| | 4.25 to 4.50 miles |
| T3-b | Algae on canal water surface covers almost 15 percent of the canal. Algae on sides of canal is growing almost up to the canal water surface. |
| T3-12 h | Canal visually free of algae. |
| T3-7 d | Slight amount of algae is growing on the water surface and along the sides of the canal. |
| T3-10 d | Algae on water surfaces covers in excess of 10 percent of the canal. Algae on the sides and bottom of canal is growing up to the water surface. Algae on growers' irrigation pump intake screens is increasing, but not problematic. |
| | 4.50 to 4.75 miles |
| T3-b | Algae on water surface covers almost 15 percent of the canal. Algae on sides of canal is growing almost up to the surface. |
| T3-12 h | Canal visually free of algae. |
| T3-7 d | Slight amount of algae is growing on the water surface and along the sides of the canal. |

TABLE 3-continued

| Treatment 3 Impact<br>Just before Treatment 3, which was 12 days after Treatment 2, (T3-b), after 12 hr. (T3-12 h), after 7 days (T3-7 d), after 10 days (T3-10 d) | |
|---|---|
| Mile/T # | Canal Description (at point (miles) along canal at T #) |
| T3-10 d | Algae on water surfaces covers in excess of 10 percent of the canal. Algae on the sides and bottom of canal is growing up to the water surface. Algae on growers' irrigation pump intake screens is increasing, but not problematic. |
| | 4.75 to 5.00 miles |
| T3-b | Algae on the water surface covers approximately 15 percent of the canal. Algae on sides and bottom of canal is growing almost up to the water surface. Algae on growers' irrigation pump intake screens is increasing, but not problematic. |
| T3-12 h | Canal visually free of algae. |
| T3-7 d | Slight amount of algae is growing on the water surface and along the sides and bottom of the canal. |
| T3-10 d | Algae on water surfaces covers about 15 percent of the canal. More algae is growing up from the sides and bottom of the canal. Algae on growers' irrigation pump intake screens is increasing, but not problematic. |
| | 5.00 to 5.25 miles |
| T3-b | Algae on the water surface covers approximately 15 percent of the canal. Algae on sides and bottom of canal is growing almost up to the water surface. Algae on growers' irrigation pump intake screens is increasing, but not problematic. |
| T3-12 h | Small amounts of discolored/dying algae are present. |
| T3-7 d | Small amount of algae is growing on the water surface. Slight amount of algae is growing along the sides and bottom of the canal. |
| T3-10 d | Algae on the water surface covers about 15 percent of the canal. More algae is growing up from the sides and bottom of the canal. Algae covering growers' irrigation pump intake screen is increasing, but not problematic. |
| | 5.25 to 5.50 miles |
| T3-b | Algae on the water surface covers more than 15 percent of the canal. Algae on sides and bottom of canal is growing almost up to the water surface. Algae on growers' irrigation pump intake screens is increasing, but not problematic. |
| T3-12 h | Small amounts of discolored/dying algae are present. |
| T3-7 d | Small amount of algae is growing on the water surface. Slight amount of algae is growing along the sides and bottom of the canal. |
| T3-10 d | Algae on the water surface covers more than 15 percent of the canal. More algae is growing up the sides and bottom of the canal. Algae covering growers' irrigation pump intake screens is increasing, but not problematic. |
| | 5.50 to 5.75 miles |
| T3-b | Algae on the water surface covers about 20 percent of the canal. More algae from the sides and bottom of the canal is reaching the water surface. |
| T3-12 h | Small amounts of discolored/dying algae are present. |
| T3-7 d | Small amount of algae is growing on the water surface and along the sides and bottom of the canal. |
| T3-10 d | Algae on the water surface covers about 20 percent of the canal. Algae from the sides and bottom of the canal is reaching the water surface and is beginning to form patches of algae. |
| | 5.75 to 6.00 miles |
| T3-b | Algae on the water surface covers about 20 percent of the canal. More algae from the sides and bottom of the canal are reaching the water surface. |
| T3-12 h | Small amounts of discolored/dying algae are adhering to the bottom and sides of the canal. |
| T3-7 d | Small amount of algae is growing on the water surface and along the sides and bottom of the canal. |
| T3-10 d | Algae on the water surface covers about 20 percent of the canal. Algae from the sides and bottom of the canal is reaching the water surface and is beginning to form patches of algae. |
| | 6.00 to 6.25 miles |
| T3-b | Algae on the water surface covers about 20 percent of the canal. More algae from the sides and bottom of the canal is reaching the water surface. |
| T3-12 h | Small amounts of discolored/dying algae are adhering to the bottom and sides of the canal. |
| T3-7 d | Small amount of algae is growing on the water surface and along the sides and bottom of the canal. |
| T3-10 d | Algae on the water surface covers about 25 percent of the canal. The algae from the sides of the canal is beginning to combine with the floating algae. |
| | 6.25 to 6.50 miles |
| T3-b | Algae on the water surface covers approximately 25 percent of the canal. Algae from the sides of the canal is beginning to combine with the floating algae. |
| T3-12 h | Small amounts of discolored/dying algae are adhering to the bottom and sides of the canal. Small patches of dead algae are floating on the canal surface covering about 1 percent of the water surface. |

TABLE 3-continued

| Mile/T # | Canal Description (at point (miles) along canal at T #) |
|---|---|
| | Treatment 3 Impact Just before Treatment 3, which was 12 days after Treatment 2, (T3-b), after 12 hr. (T3-12 h), after 7 days (T3-7 d), after 10 days (T3-10 d) |
| T3-7 d | Small amount of algae is growing on the water surface and along the sides and bottom of the canal. |
| T3-10 d | Algae on the water surface covers about 25 percent of the canal. The algae from the sides of the canal is beginning to combine with the floating algae. |
| | 6.50 to 6.75 miles |
| T3-b | Algae on the water surface covers approximately 25 percent of the canal. Algae from the sides of the canal is beginning to combine with the floating algae. |
| T3-12 h | Small amounts of discolored/dying algae are adhering to the bottom and sides of the canal. Small patches of dead algae are floating on the canal surface covering about 1 percent of the water surface. |
| T3-7 d | Small amount of algae is growing on the water surface and along the sides and bottom of the canal. |
| T3-10 d | Algae on the water surface covers about 25 percent of the canal. The algae from the sides of the canal is beginning to combine with the floating algae. |
| | 6.75 to 7.00 miles |
| T3-b | Algae on the water surface covers approximately 25 percent of the canal. Algae from the sides of the canal is beginning to combine with the floating algae. |
| T3-12 h | Small amounts of discolored/dying algae are adhering to the bottom and sides of the canal. Small patches of dead algae are floating on the canal and are covering approximately 2 to 3 percent of the canal. |
| T3-7 d | Slight patches of algae are floating on the water surface. Small amount of algae is growing along the sides and bottom of the canal. |
| T3-10 d | Algae on the water surface covers about 25 percent of the canal. The algae from the sides of the canal is beginning to combine with the floating algae. |

The present invention in a broad embodiment is a method of treating an agricultural-water canal to decompose organic debris in the agricultural-water canal by a controlled delivery of biocide particles to the surface of water in the agricultural-water canal comprising the steps of: entraining biocide particles in a gaseous stream to form a biocide-laden gaseous stream; and then scattering the biocide particles across the surface of the water by propelling the biocide-laden gaseous stream to the surface of the water, whereat the biocide particles are released from the gaseous stream. Preferably the scattering provides a sufficiently consistent distribution of the biocide particles across the surface of the water.

In various preferred embodiments of such method, separately and in combination, the gaseous stream is an air stream and the biocide particles are calcium hypochlorite particles of from 1.0 mm to 0.1 mm. When the surface of the water is at least partially covered with floating organic debris, the biocide-laden gaseous stream is preferably propelled with sufficient force to embed the biocide (calcium hypochlorite) particles in the floating organic debris. The biocide-laden gaseous stream is preferably propelled at a linear velocity of from 40 to 180 miles per hour, and when the biocide particles are calcium hypochlorite particles, such linear velocity is normally sufficient to embed the particles in floating organic debris. Preferably a biologically-remedial amount of the biocide, such as calcium hypochlorite, is delivered to the water of the agricultural-water canal, and preferably the scattering of the biocide particles is at least partially targeted whereby a higher concentration of biocide (calcium hypochlorite) particles is delivered to a target area having a higher loading of organic debris, such as algae mats along the sides of the canal. Also preferably, the biocide particles are calcium hypochlorite particles that, after the release from the gaseous stream, are consumed, or at least partially consumed, in the decomposition of the organic debris, and unconsumed calcium hypochlorite dissipates to benign byproducts as discussed above.

In further preferred embodiments, the biocide-laden gaseous stream is propelled to the surface of the water simultaneously from a plurality of ports, which preferably are disposed overhead of the surface of the water and more preferably, are disposed at a plurality of angles and/or while the ports are being translated along the agricultural-water canal.

In other broad embodiments, the present invention is a device for treating an agricultural-water canal to decompose organic debris in the agricultural-water canal by the aforesaid method. Such device comprises: (a) a conduit; (b) a gas blower adapted to form a gaseous stream and discharge the gaseous stream to the conduit; (c) a feed hopper open to the conduit at a feed point downstream of the gas blower and adapted to feed biocide particles to the gaseous stream so as to form a biocide-laden gaseous stream; and (d) at least one port (preferably a plurality of ports) open to the conduit, wherein the conduit is adapted to channel the biocide-laden gaseous stream to the port, and wherein the port is adapted to direct and propel the biocide-laden gaseous stream to the surface of water in the agricultural-water canal (preferably from a position overhead of the water).

In preferred embodiments, the gas blower is an air blower and/or the feed hopper is adapted to feed calcium hypochlorite particles to the gaseous stream so as to form such biocide-laden gaseous stream.

In other preferred embodiments, the gas blower, the conduit and the port(s) are adapted to propel the biocide-laden gaseous stream to the surface of the water at a linear velocity of from 40 to 180 miles per hour.

In further preferred embodiments, the port(s) has a discharge aperture having an adjustable cross-sectional area, so as to control the volume of the gaseous stream passing therethrough, and thereby control the dosage of biocide being released to the canal water. The port(s) preferably has a discharge aperture and the port is adapted for directional adjustment of the discharge aperture so as to control the direction in which the gaseous stream is propelled to the canal water.

In preferred embodiments, the device further includes (a) a spindle having a plurality of spokes disposed within the feed hopper and adapted to reduce the particle sizes of the biocide particles upstream of the conduit and/or a venturi disposed within the conduit at the feed point and adapted to facilitate the entrainment of the biocide particles in the gaseous air stream.

In particularly preferred embodiments, the device for treating an agricultural-water canal to decompose organic debris in the agricultural-water canal includes a mobile unit having a first side, wherein the gas blower and the hopper are mounted on the mobile unit, and wherein the conduit is adapted to project from the first side of the mobile unit a sufficient distance to dispose the port overhead of the water. In such an embodiment, the mobile unit is preferably adapted to travel along a side of the agricultural-water canal, and the ports are adapted to simultaneously direct and propel the biocide-laden gaseous stream to the surface of water in the agricultural-water canal from the plurality of positions overhead of the surface of the water while the mobile unit is traveling along the side of the agricultural-water canal. In other preferred embodiments, the device includes a boom, the conduit is mounted on the boom, and the boom is adapted to project from the first side of the mobile unit a sufficient distance to dispose the plurality of ports at a plurality of positions overhead of the water so that they simultaneously direct and propel the biocide-laden gaseous stream to the surface of water in the agricultural-water canal from the plurality of positions overhead of the surface of the water while the mobile unit is traveling along the side of the agricultural-water canal.

In other preferred embodiments, the boom is an articulated boom which is translatable between an extended mode and a collapsed mode, wherein the boom is adapted (a) to project from the first side of the mobile unit a sufficient distance to dispose the plurality of ports at a plurality of positions overhead of the water in the extended mode and (b) to accordion fold (form an accordion fold) against the first side of the mobile unit in the collapsed mode, which normally would be done manually, after removal of the conduit, and while the mobile unit is stationary.

In further preferred embodiments, such articulated boom has a proximal and distal end and the mobile unit includes a pulley having a line running to a point on the boom between the proximal and distal ends. In such preferred embodiments, the boom is (also) adapted to, in the extended mode, (a) project from the first side of the mobile unit a sufficient distance to dispose the plurality of ports at a plurality of positions overhead of the water, while the proximal end is lodged against the first side of the mobile unit, and (b) pivot on the proximal end while being swung between an upwardly-angled position and a sideward position by the pulley while the mobile unit is traveling along the side of the agricultural-water canal. As discussed and illustrated above, such pivotal raising of the boom, normally with the conduit attached, permits the mobile unit to continue traveling along the side of a canal while obstacles along the canal are avoided by so raising the boom and the attached conduit.

In other preferred embodiments, the mobile unit has at least one window adapted for viewing the canal from inside the mobile unit while the mobile unit is traveling along the side of the agricultural-water canal and/or a sufficient storage capacity to carry a sufficient amount of biocide particles for the decomposition of the organic debris along the entire length of the canal. Using such a mobile unit, the mobile unit can traverse, and treat, the entire length of a canal without stopping to reload biocide particles, without stopping to determine the target dosages, and without stopping to avoid obstacles in and around the canal. The articulated boom preferably is formed of a plurality of detachable sections, which permits a boom of a suitable length for a given canal to be readily assembled from various sections of the same or different lengths.

The present invention in broad embodiments also includes a method for treating an agricultural-water canal to decompose organic debris in the agricultural-water canal using the device of the present invention (particularly as that device is described immediately above). Such a method comprises the steps of: (a) forming a gaseous stream using the gas blower; (b) discharging the gaseous stream to the conduit; (c) feeding biocide particles from the feed hopper to the gas stream at the feed point to form a biocide-laden gaseous stream in the conduit whereby the conduit channels the biocide-laden gaseous stream to the port(s); and (d) directing and propelling the biocide-laden gaseous stream through the port to the surface of water in the agricultural-water canal.

In preferred embodiments of such method, (a) the gas blower is an air blower and an air stream is formed using the air blower and/or (b) the biocide particles are calcium hypochlorite particles and the biocide-laden gaseous stream which is formed is a calcium hypochlorite-laden gaseous stream.

In other preferred embodiments of such method, the biocide-laden gaseous stream is propelled to the surface of water in the agricultural-water canal at a linear velocity of from 40 to 180 miles per hour.

In further preferred embodiments of the invention, the biocide dosage, i.e., the amount of biocide per unit area that is being delivered to the canal, is controlled in one or more ways. In one embodiment, the port(s) has a discharge aperture having an adjustable cross-sectional area, and the amount of the biocide particles that will be propelled through the port is controlled by adjusting the cross-sectional area of the discharge aperture of the port. In another embodiment, the port(s) is adapted for directional adjustment of the discharge aperture and the biocide dosage at a given target area is controlled by adjusting the direction at which the biocide particles will be propelled through the port(s) by adjusting the directional angle of the discharge aperture of the port. (This control feature is particularly effective to target areas of high organic debris fouling, such as along the side of a canal.) In another preferred embodiment, the biocide dosage is controlled by the discharge rate (orifice openings) of the hopper as the biocide is added to the gas stream.

In other preferred embodiments, prior to the step of feeding biocide particles from the feed hopper to the gas stream downstream of the gas blower, the particle sizes of the biocide are reduced, and preferably have their particle-size distribution range narrowed, using the spindle disposed within the feed hopper ahead of the feed point.

This method preferably uses a device which includes a mobile unit, wherein the gas blower and the hopper are mounted on the mobile unit, and the conduit is adapted to project from the side of the mobile unit (the side closest to the canal) a sufficient distance to dispose the port(s) overhead of the water, wherein the biocide-laden gaseous stream is simultaneously directed and propelled to the surface of water in the agricultural-water canal from the plurality of positions overhead of the surface of the water while the mobile unit is traveling along the side of the agricultural-water canal. In this and other preferred embodiments, the biocide particles are preferably fed to the feed hopper from the inside of the mobile unit.

In other preferred embodiments, the device includes a boom, particularly wherein the conduit is mounted on the boom. In such embodiments, the biocide-laden gaseous stream is simultaneously directed and propelled to the surface of water in the agricultural-water canal while the boom and the conduit are projecting from the first side of the mobile unit a sufficient distance to dispose the plurality of ports at a plurality of positions overhead of the water, and while the mobile unit is traveling along the side of the agricultural-water canal.

The method preferably, when the conduit is mounted on the boom, includes the steps of (a) simultaneously directing and propelling the biocide-laden gaseous stream to the surface of the water in the agricultural-water canal from the plurality of positions overhead of the surface of the water while the boom, with the attached conduit, is in the extended mode, and while the mobile unit is traveling along the side of the agricultural-water canal, (b) detaching the conduit from the boom, and (c) translating the boom from the extended mode to the collapsed mode by accordion folding (forming an accordion fold) the boom against the first side of the mobile unit. The latter two steps would of course normally be performed after the mobile unit is halted, and typically after the entire length of a canal has been treated. The mobile unit is thereby compacted for travel to another site.

In further preferred embodiments, when the device further includes an articulated boom having a proximal and distal end, and a pulley having a line running to a point on the boom between the proximal and distal ends, the steps of (a) simultaneously directing and propelling the biocide-laden gaseous stream to the surface of water in the agricultural-water canal while the boom, in the extended mode, is disposed in a sideward position, and (b) swinging the boom and the conduit between the sideward position and an upwardly-angled position and then a sideward position by the pulley while the mobile unit is traveling along the side of the agricultural-water canal. These steps permit obstacles along the canal to be avoided without halting the mobile unit and without in any way disassembling the boom and attached conduit. When the obstacle has been passed, the boom and the attached conduit are merely swung down back to the sideward position.

The method also preferably includes viewing the biological demand for biocide in a first section of the agricultural-water canal and determining a target dosage of biocide based on the viewing from the inside of the mobile unit while the mobile unit is traveling along the side of the agricultural-water canal. As noted above, the mobile unit preferably has at least one viewing window so that an operator can view the canal and make such determination from within the mobile unit. In preferred embodiment, the operator is doing so while the mobile unit is traveling along the side of the agricultural-water canal. Preferably the operator is also controlling the dosage of biocide based on such determination, by the method(s) of adjusting the speed of the mobile unit along the side of the agricultural-water canal (by himself or through a driver) and/or adjusting the concentration of biocide in the biocide-laden gaseous stream. Preferably the viewings and determinations are done repetitively and the adjustments are made intermittently, and as required.

Further, as discussed above, in preferred embodiments of the method, the biocide-laden gaseous stream is propelled through the port to the surface of water in the agricultural-water canal with a sufficient linear velocity to embed the biocide particles, such as calcium hypochlorite particles, in the floating organic debris. In preferred embodiments of the method, the biocide-laden gaseous stream is propelled through the port to the surface of water in the agricultural-water canal with a sufficient linear velocity to impregnate the floating organic debris with calcium hypochlorite particles.

While the foregoing written description of the invention enables one of ordinary skill to make and use what is considered presently to be the best mode thereof, those of ordinary skill will understand and appreciate the existence of variations, combinations, and equivalents of the specific embodiment, method, and examples herein. The invention should therefore not be limited by the above described embodiment, method, and examples, but by all embodiments and methods within the scope and spirit of the invention as claimed.

We claim:

1. A method for treating an agricultural-water canal to decompose organic debris in said agricultural-water canal using a device having a conduit, an air blower adapted to form an air stream and discharge said air stream to said conduit, a feed hopper open to said conduit at a feed point downstream of said air blower and adapted to feed calcium hypochlorite particles to said gaseous stream so as to form a calcium hypochlorite-laden air stream, and a port open to said conduit downstream of said feed point, wherein said conduit is adapted to channel said calcium hypochlorite-laden air stream to said port, and wherein said port is adapted to direct and propel said calcium hypochlorite-laden air stream to the surface of water in said agricultural-water canal, said method comprising the steps of:

forming an air stream using said air blower;

discharging said air stream to said conduit;

feeding calcium hypochlorite particles having a particle size of less than 1 mm from said feed hopper to said air stream at said feed point to form a calcium hypochlorite-laden air stream in said conduit whereby said conduit channels said calcium hypochlorite-laden air stream to said port;

embedding said calcium hypochlorite particles in organic debris in water in said agricultural-water canal by directing and propelling said calcium hypochlorite-laden air stream through said port to the surface of water in said agricultural-water canal at a linear velocity of from 40 to 180 miles per hour.

2. The method for treating an agricultural-water canal to decompose organic debris in said agricultural-water canal according to claim 1, wherein said port has a discharge aperture having an adjustable cross-sectional area, further including, prior to said step of directing and propelling said calcium hypochlorite-laden air stream through said port to the surface of water in said agricultural-water canal, the step of:

adjusting the amount of said calcium hypochlorite particles that will be propelled through said port by adjusting said cross-sectional area of said discharge aperture of said port.

3. The method for treating an agricultural-water canal to decompose organic debris in said agricultural-water canal according to claim 1, wherein said port has a discharge aperture and said port is adapted for directional adjustment of said discharge aperture, further including, prior to said step of directing and propelling said calcium hypochlorite-laden air stream through said port to the surface of water in said agricultural-water canal, the step of:

adjusting the direction at which said calcium hypochlorite particles will be propelled through said port by adjusting said cross-sectional area of said discharge aperture of said port.

4. The method for treating an agricultural-water canal to decompose organic debris in said agricultural-water canal according to claim 1, wherein said device further includes a plurality of ports open to said conduit and adapted to simultaneously direct and propel said calcium hypochlorite-laden air stream to said surface of said water, further including, in said step of directing and propelling said calcium hypochlorite-laden air stream through said port to the surface of water in said agricultural-water canal, the step of:

simultaneously directing and propelling said calcium hypochlorite-laden air stream through said ports to the surface of water in said agricultural-water canal.

5. The method for treating an agricultural-water canal to decompose organic debris in said agricultural-water canal according to claim 1, wherein said device further includes a plurality of ports open to said conduit and adapted to simultaneously direct and propel said calcium hypochlorite-laden air stream to said surface of said water, further including, in said step of directing and propelling said calcium hypochlorite-laden air stream through said port to the surface of water in said agricultural-water canal, the step of:

simultaneously directing and propelling said calcium hypochlorite-laden air stream through said ports to the surface of water in said agricultural-water canal from a position overhead of said surface of said water.

6. The method for treating an agricultural-water canal to decompose organic debris in said agricultural-water canal according to claim 1, wherein said calcium hypochlorite particles have a particle size distribution and wherein said device further includes a spindle having a plurality of spokes disposed within said feed hopper and adapted to reduce and narrow said particle size distribution of said calcium hypochlorite particles upstream of said conduit, further including, prior to the step of feeding said calcium hypochlorite particles from said feed hopper to said air stream downstream of said air blower, the step of:

reducing and narrowing said particle size distribution of said calcium hypochlorite using said spindle disposed within said feed hopper ahead of said feed point.

7. The method for treating an agricultural-water canal to decompose organic debris in said agricultural-water canal according to claim 1, wherein said device further includes a mobile land unit having an inside and a first side, wherein said air blower and said hopper are mounted on said mobile land unit, and wherein said conduit is adapted to project from said first side of said mobile land unit a sufficient distance to dispose said port overhead of said water, further including, in the step of feeding said calcium hypochlorite particles from said feed hopper to said air stream at said feed point to form a calcium hypochlorite-laden air stream in said conduit, the step of:

feeding said calcium hypochlorite particles to said feed hopper from said inside of said mobile land unit.

8. The method for treating an agricultural-water canal to decompose organic debris in said agricultural-water canal according to claim 1, wherein said device further includes a mobile land unit having a first side and a plurality of ports open to said conduit, wherein said air blower and said hopper are mounted on said mobile land unit, wherein said mobile land unit is adapted to travel along a side of said agricultural-water canal, wherein said conduit is adapted to project from said first side of said mobile land unit a sufficient distance to dispose said plurality of ports at a plurality of positions overhead of said water, and wherein said ports are adapted to simultaneously direct and propel said calcium hypochlorite-laden air stream to the surface of water in said agricultural-water canal from said plurality of positions overhead of said surface of said water while said mobile land unit is traveling along said side of said agricultural-water canal, further including, in the step of directing and propelling said calcium hypochlorite-laden air stream through said port to the surface of water in said agricultural-water canal, the step of:

simultaneously directing and propelling said calcium hypochlorite-laden air stream to the surface of water in said agricultural-water canal from said plurality of positions overhead of said surface of said water while said mobile land unit is traveling along said side of said agricultural-water canal.

9. The method for treating an agricultural-water canal to decompose organic debris in said agricultural-water canal according to claim 1, wherein said device further includes a mobile land unit having a first side, a plurality of ports open to said conduit, and a boom, wherein said air blower and said hopper are mounted on said mobile land unit, wherein said mobile land unit is adapted to travel along a side of said agricultural-water canal, wherein said conduit is mounted on said boom, wherein said boom is adapted to project from said first side of said mobile land unit a sufficient distance to dispose said plurality of ports at a plurality of positions overhead of said water, and wherein said ports are adapted to simultaneously direct and propel said calcium hypochlorite-laden air stream to the surface of water in said agricultural-water canal from said plurality of positions overhead of said surface of said water while said mobile land unit is traveling along said side of said agricultural-water canal, further including, in the step of directing and propelling said calcium hypochlorite-laden air stream through said port to the surface of water in said agricultural-water canal, the step of:

simultaneously directing and propelling said calcium hypochlorite-laden air stream to the surface of water in said agricultural-water canal from said plurality of positions overhead of said surface of said water while said boom and said conduit are projecting from said first side of said mobile land unit a sufficient distance to dispose said plurality of ports at a plurality of positions overhead of said water and while said mobile land unit is traveling along said side of said agricultural-water canal.

10. The method for treating an agricultural-water canal to decompose organic debris in said agricultural-water canal according to claim 1, said device further including a mobile land unit having a first side, a plurality of ports open to said conduit and an articulated boom, wherein said air blower and said hopper are mounted on said mobile land unit, wherein said mobile land unit is adapted to travel along a side of said agricultural-water canal, wherein said conduit is adapted to be mounted on said boom, wherein said boom is translatable between an extended mode and a collapsed mode, wherein said boom is adapted to (a) project from said first side of said mobile land unit a sufficient distance to dispose said plurality of ports at a plurality of positions overhead of said water in said extended mode and (b) accordion fold against said first side of said mobile land unit in said collapsed mode, and wherein said ports are adapted to simultaneously direct and propel said calcium hypochlorite-laden air stream to the surface of water in said agricultural-water canal from said plurality of positions overhead of said surface of said water while said mobile land unit is traveling along said side of said agricultural-water canal, further including, in and after the step of directing and propelling said calcium hypochlorite-laden air stream through said port to the surface of water in said agricultural-water canal, the steps of:

simultaneously directing and propelling said calcium hypochlorite-laden air stream to the surface of water in said agricultural-water canal from said plurality of positions overhead of said surface of said water while said boom in said extended mode and said conduit are projecting from said first side of said mobile land unit a sufficient distance to dispose said plurality of ports at a plurality of positions overhead of said water and while said mobile land unit is traveling along said side of said agricultural-water canal;

detaching said conduit from said boom; and translating said boom from said extended mode to said collapsed mode by accordion folding said boom against said first side of said mobile land unit.

11. The method for treating an agricultural-water canal to decompose organic debris in said agricultural-water canal according to claim 1, wherein said device further includes a mobile land unit having a first side, a plurality of ports open to said conduit, an articulated boom having a proximal and distal end and a pulley having a line running to a point on said boom between said proximal and distal ends, wherein said air blower and said hopper are mounted on said mobile land unit, wherein said mobile land unit is adapted to travel along a side of said agricultural-water canal, wherein said conduit is adapted to be mounted on said boom, wherein said boom is adapted to be translated between an extended mode and a collapsed mode, wherein said boom is adapted to, in said extended mode, (a) project from said first side of said mobile land unit a sufficient distance to dispose said plurality of ports at a plurality of positions overhead of said water, while said proximal end is lodged against said first side of said mobile land unit and (b) pivot on said proximal end while being swung between an upwardly-angled position and a sideward position by said pulley, while said mobile land unit is traveling along said side of said agricultural-water canal, and wherein said ports are adapted to simultaneously direct and propel said calcium hypochlorite-laden air stream to the surface of water in said agricultural-water canal from said plurality of positions overhead of said surface of said water while said mobile land unit is traveling along said side of said agricultural-water canal, further including, in and after the step of directing and propelling said calcium hypochlorite-laden air stream through said port to the surface of water in said agricultural-water canal, the steps of:

simultaneously directing and propelling said calcium hypochlorite-laden air stream to the surface of water in said agricultural-water canal from said plurality of positions overhead of said surface of said water while said boom in said extended mode and said conduit are projecting from said first side of said mobile land unit a sufficient distance to dispose said plurality of ports at a plurality of positions overhead of said water and while said mobile land unit is traveling along said side of said agricultural-water canal; and swinging said boom and said conduit between a sideward position and an upwardly-angled position and then a sideward position by said pulley while said mobile land unit is traveling along said side of said agricultural-water canal.

12. The method for treating an agricultural-water canal to decompose organic debris in said agricultural-water canal according to claim 1, wherein said device further includes a mobile land unit adapted to travel along a side of said agricultural-water canal, said mobile land unit having an inside, a first side and at least one window adapted for viewing said canal from inside said mobile land unit while said mobile land unit is traveling along said side of said agricultural-water canal, a plurality of ports open to said conduit, and a boom, wherein said air blower and said hopper are mounted on said mobile land unit, wherein said conduit is mounted on said boom, wherein said boom is adapted to project from said first side of said mobile land unit a sufficient distance to dispose said plurality of ports at a plurality of positions overhead of said water, and wherein said ports are adapted to simultaneously direct and propel said calcium hypochlorite-laden air stream to the surface of water in said agricultural-water canal from said plurality of positions overhead of said surface of said water while said mobile land unit is traveling along said side of said agricultural-water canal, further including, in the step of directing and propelling said calcium hypochlorite-laden air stream through said port to the surface of water in said agricultural-water canal, the steps of:

while said mobile land unit is traveling along said side of said agricultural-water canal, viewing the biological demand for biocide in a first section of said agricultural-water canal and determining a target dosage of biocide based on said viewing from said inside of said mobile land unit;

adjusting the concentration of calcium hypochlorite in said calcium hypochlorite-laden air stream based on said target dosage; and while said boom and said conduit are projecting from said first side of said mobile land unit a sufficient distance to dispose said plurality of ports at a plurality of positions overhead of said water and while said mobile land unit is traveling along said side of said agricultural-water canal, simultaneously directing and propelling said calcium hypochlorite-laden air stream to the surface of water in said agricultural-water canal from said plurality of positions overhead of said surface of said water.

13. The method for treating an agricultural-water canal to decompose organic debris in said agricultural-water canal according to claim 1, wherein said device further includes a mobile land unit adapted to travel along a side of said agricultural-water canal, said mobile land unit having an inside, a first side and at least one window adapted for viewing said canal from inside said mobile land unit while said mobile land-unit is traveling along said side of said agricultural-water canal, a plurality of ports open to said conduit, and a boom, wherein said air blower and said hopper are mounted on said mobile land unit, wherein said conduit is mounted on said boom, wherein said boom is adapted to project from said first side of said mobile land unit a sufficient distance to dispose said plurality of ports at a plurality of positions overhead of said water, and wherein said ports are adapted to simultaneously direct and propel said calcium hypochlorite-laden air stream to the surface of water in said agricultural-water canal from said plurality of positions overhead of said surface of said water while said mobile land unit is traveling along said side of said agricultural-water canal, further including, in the step of directing and propelling said calcium hypochlorite-laden air stream through said port to the surface of water in said agricultural-water canal, the steps of:

while said mobile land unit is traveling along said side of said agricultural-water canal, viewing the biological demand for biocide in a first section of said agricultural-water canal and determining a target dosage of biocide based on said viewing from said inside of said mobile land unit;

adjusting the speed of said mobile land unit along said side of said agricultural-water canal based on said target dosage; and while said boom and said conduit are projecting from said first side of said mobile land unit a sufficient distance to dispose said plurality of ports at a plurality of positions overhead of said water and while said mobile land unit is traveling along said side of said agricultural-water canal, simultaneously directing and propelling said calcium hypochlorite-laden air stream to the surface of water in said agricultural-water canal from said plurality of positions overhead of said surface of said water.

14. The method for treating an agricultural-water canal to decompose organic debris in said agricultural-water canal according to claim 1, wherein said device further includes a mobile land unit adapted to travel along a side of said agricultural-water canal, said mobile land unit having an inside, a first side and at least one window adapted for viewing said canal from inside said mobile land unit while said mobile land unit is traveling along said side of said agricultural-water canal, a plurality of ports open to said conduit, and a boom, wherein said air blower and said hopper are mounted on said mobile land unit, wherein said conduit is mounted on said boom, wherein said boom is adapted to project from said first side of said mobile land unit a sufficient distance to dispose said plurality of ports at a plurality of positions overhead of said water, and wherein said ports are adapted to simultaneously direct and propel said calcium hypochlorite-laden air stream to the surface of water in said agricultural-water canal from said plurality of positions overhead of said surface of said water while said mobile land unit is traveling along said side of said agricultural-water canal, further including, in the step of directing and propelling said calcium hypochlorite-laden air stream through said port to the surface of water in said agricultural-water canal, the steps of:

while said mobile land unit is traveling along said side of said agricultural-water canal, viewing the biological demand for biocide in a first section of said agricultural-water canal and determining a target dosage of biocide based on said viewing from said inside of said mobile land unit;

adjusting the concentration of calcium hypochlorite in said calcium hypochlorite-laden air stream and adjusting the speed of said mobile land unit along said side of said agricultural-water canal based on said target dosage; and while said boom and said conduit are projecting from said first side of said mobile land unit a sufficient distance to dispose said plurality of ports at a plurality of positions overhead of said water and while said mobile land unit is traveling along said side of said agricultural-water canal, simultaneously directing and propelling said calcium hypochlorite-laden air stream to the surface of water in said agricultural-water canal from said plurality of positions overhead of said surface of said water.

15. The method for treating an agricultural-water canal to decompose organic debris in said agricultural-water canal according to claim 1, wherein said device further includes a mobile land unit adapted to travel along a side of said agricultural-water canal, said mobile land unit having an inside, a first side and at least one window adapted for viewing said canal from inside said mobile land unit while said mobile land unit is traveling along said side of said agricultural-water canal, a plurality of ports open to said conduit, and a boom, wherein said air blower and said hopper are mounted on said mobile land unit, wherein said conduit is mounted on said boom, wherein said boom is adapted to project from said first side of said mobile land unit a sufficient distance to dispose said plurality of ports at a plurality of positions overhead of said water, and wherein said ports are adapted to simultaneously direct and propel said calcium hypochlorite-laden air stream to the surface of water in said agricultural-water canal from said plurality of positions overhead of said surface of said water while said mobile land unit is traveling along said side of said agricultural-water canal, further including, in the step of directing and propelling said calcium hypochlorite-laden air stream through said port to the surface of water in said agricultural-water canal, the steps of:

while said mobile land unit is traveling along said side of the length of said agricultural-water canal, repetitively viewing the biological demand for biocide in adjacent sections of said agricultural-water canal and repetitively determining target dosages of biocide based on said viewings from said inside of said mobile land unit;

intermittently adjusting the concentration of biocide in said calcium hypochlorite-laden air stream based on said target dosage;

intermittently adjusting the speed of said mobile land unit along said side of said agricultural-water canal based on said target dosage; and while said boom and said conduit are projecting from said first side of said mobile land unit a sufficient distance to dispose said plurality of ports at a plurality of positions overhead of said water and while said mobile land unit is traveling along said side of said agricultural-water canal, simultaneously directing and propelling said calcium hypochlorite-laden air stream to the surface of water in said agricultural-water canal from said plurality of positions overhead of said surface of said water.

* * * * *